(12) United States Patent
Aquino et al.

(10) Patent No.: US 10,849,713 B2
(45) Date of Patent: *Dec. 1, 2020

(54) METHOD AND APPARATUS TO ACCOUNT FOR TRANSPONDER TAGGED OBJECTS USED DURING CLINICAL PROCEDURES, EMPLOYING A TROCAR

(71) Applicant: Covidien LP, Mansfield, MA (US)

(72) Inventors: Allan Aquino, Longmont, CO (US); Kim Brandt, Loveland, CO (US); Andy Buersmeyer, Ft. Collins, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/279,403

(22) Filed: Feb. 19, 2019

(65) Prior Publication Data

US 2019/0298484 A1 Oct. 3, 2019

Related U.S. Application Data

(60) Provisional application No. 62/648,534, filed on Mar. 27, 2018, provisional application No. 62/648,539, filed on Mar. 27, 2018.

(51) Int. Cl.
*A61B 90/98* (2016.01)
*A61B 34/20* (2016.01)
(Continued)

(52) U.S. Cl.
CPC .............. *A61B 90/98* (2016.02); *A61B 17/34* (2013.01); *A61B 17/3421* (2013.01);
(Continued)

(58) Field of Classification Search
None
See application file for complete search history.

(56) References Cited

U.S. PATENT DOCUMENTS 5,211,129 A * 5/1993 Taylor .............. G06K 19/07758
119/215
6,026,818 A 2/2000 Blair et al.
(Continued)

FOREIGN PATENT DOCUMENTS

WO 2016156201 10/2016

OTHER PUBLICATIONS

U.S. Appl. No. 62/182,294, filed Jun. 19, 2015.
(Continued)

*Primary Examiner* — Brent Swarthout
(74) *Attorney, Agent, or Firm* — Carter, DeLuca & Farrell LLP

(57) ABSTRACT

Medical procedure related objects (e.g., instruments, supplies) tagged with transponders (e.g., RFID transponders, dumb transponders) are accounted for via an accounting system using a number of antennas and interrogators/readers. The antennas and interrogators/readers are included on a cannula of the trocar so the tagged medical procedure related objects passing through the cannula are detected. A first set of antennas and RFID interrogator(s) interrogate a first portion of the cannula, such as proximate a proximal end at which the medical procedure related objects are introduced to the cannula. A second set of antennas and RFID interrogator(s) interrogate a second portion of the cannula, such as proximate a distal end at which objects exit the cannula for use in a medical procedure. A data store may maintain information including a current status or count of each supply, for instance, as entering or exiting the cannula.

6 Claims, 12 Drawing Sheets

(51) Int. Cl.
   *A61B 90/00* (2016.01)
   *A61B 17/34* (2006.01)
   *A61B 17/00* (2006.01)

(52) U.S. Cl.
   CPC .............. *A61B 34/20* (2016.02); *A61B 90/39* (2016.02); *A61B 2017/00115* (2013.01); *A61B 2017/00482* (2013.01); *A61B 2034/2051* (2016.02); *A61B 2090/0804* (2016.02); *A61B 2090/0805* (2016.02); *A61B 2090/0811* (2016.02); *A61B 2090/3958* (2016.02)

(56) References Cited

U.S. PATENT DOCUMENTS

| | | |
|---|---|---|
| 6,650,143 B1 | 11/2003 | Peng |
| 6,667,902 B2 | 12/2003 | Peng |
| 6,671,040 B2 | 12/2003 | Fong et al. |
| 6,700,151 B2 | 3/2004 | Peng |
| 6,766,960 B2 | 7/2004 | Peng |
| 6,777,757 B2 | 8/2004 | Peng et al. |
| 6,791,891 B1 | 9/2004 | Peng et al. |
| 6,798,693 B2 | 9/2004 | Peng |
| 6,822,888 B2 | 11/2004 | Peng |
| 6,856,540 B2 | 2/2005 | Peng et al. |
| 6,898,116 B2 | 5/2005 | Peng |
| 6,940,751 B2 | 9/2005 | Peng et al. |
| 6,956,258 B2 | 10/2005 | Peng |
| 6,972,986 B2 | 12/2005 | Peng et al. |
| 6,992,925 B2 | 1/2006 | Peng |
| 7,031,209 B2 | 4/2006 | Wang et al. |
| 7,042,722 B2 | 5/2006 | Suzuki et al. |
| 7,269,047 B1 | 9/2007 | Fong et al. |
| 7,471,541 B2 | 12/2008 | Fong et al. |
| 7,609,538 B1 | 10/2009 | Lee et al. |
| 7,696,877 B2 | 4/2010 | Barnes et al. |
| 7,898,420 B2 | 3/2011 | Blair et al. |
| 7,981,092 B2 | 7/2011 | Duke |
| 8,111,162 B2 | 2/2012 | Barnes et al. |
| 8,354,931 B2 | 1/2013 | Blair |
| 8,358,212 B2 | 1/2013 | Blair |
| 8,710,957 B2 | 4/2014 | Blair et al. |
| 9,136,597 B2 | 9/2015 | Blair |
| 9,514,341 B2 | 12/2016 | Blair et al. |
| 9,592,962 B1 | 3/2017 | Lee |
| 9,690,963 B2 | 6/2017 | Buhler et al. |
| 9,717,565 B2 | 8/2017 | Blair |
| 9,872,732 B2 | 1/2018 | Blair |
| 10,193,209 B2 | 1/2019 | Blair |
| 10,285,775 B2 | 5/2019 | Blair |
| 2004/0250819 A1 | 12/2004 | Blair et al. |
| 2007/0285249 A1 | 12/2007 | Blair et al. |
| 2008/0294036 A1* | 11/2008 | Hoi ........................ A61B 5/062 600/424 |
| 2010/0108079 A1 | 5/2010 | Blair |
| 2010/0109848 A1 | 5/2010 | Blair et al. |
| 2011/0004276 A1 | 1/2011 | Blair et al. |
| 2011/0181394 A1 | 7/2011 | Blair |
| 2013/0016021 A1 | 1/2013 | Blair |
| 2014/0303580 A1 | 10/2014 | Blair |
| 2015/0216610 A1 | 8/2015 | Augustine |
| 2015/0272688 A1 | 10/2015 | Blair et al. |
| 2016/0210548 A1 | 7/2016 | Blair |
| 2017/0169172 A1 | 6/2017 | Blair et al. |
| 2019/0151044 A1* | 5/2019 | Black ..................... A61B 17/34 |

OTHER PUBLICATIONS

U.S. Appl. No. 62/164,412, filed May 20, 2015.
U.S. Appl. No. 62/360,864 (now U.S. Pat. No. 16/316,986) filed Jul. 11, 2016 and entitled "Method and Apparatus to account for Transponder tagged objects used during clinical procedures, employing a shielded receptacle".
U.S. Appl. No. 62/360,866 (now U.S. Pat. No. 16/316,979) filed Jul. 11, 2016 and entitled Method and Apparatus to account for Transponder tagged objects used during clinical procedures employing a shielded receptacle with antenna.
U.S. Appl. No. 62/360,868 (now U.S. Pat. No. 16/316,904) filed Jul. 11, 2016 and entitled "Method and Apparatus to account for Transponder tagged objects used during clinical procedures, for example Including count in and/or count out and presence detection".
Extended European Search Report dated Aug. 13, 2019 corresponding to counterpart Patent Application EP 19165327.8.

* cited by examiner

METHOD AND APPARATUS TO ACCOUNT FOR TRANSPONDER TAGGED OBJECTS USED DURING CLINICAL PROCEDURES, EMPLOYING A TROCAR

CROSS-REFERENCE TO RELATED APPLICATIONS

This application claims the benefit of and priority to U.S. Provisional Patent Application Nos. 62/648,534 and 62/648,539 filed Mar. 27, 2018, the entire disclosures of which are incorporated by reference herein.

TECHNICAL FIELD

The present disclosure generally relates to accounting for transponder tagged medical or clinical procedure objects or items, for instance disposable gauze or sponges, and/or medical or clinical instruments typically employed in a medical or clinical environment in which medical or clinical procedures are performed.

BACKGROUND

Description of the Related Art

It is important to determine whether objects or items associated with a medical or clinical procedure are present or unintentionally retained in a patient's body before completion of a medical or clinical procedure. The medical or clinical procedure may, for example, take the form of a surgery or childbirth delivery. Such objects or items may take a variety of forms used in medical or clinical procedures. For example, the objects or items may take the form of instruments, for instance scalpels, scissors, forceps, hemostats, and/or clamps, which may be reusable after sterilization or alternatively may be single-use disposable objects or items. Also for example, the objects or items may take the form of related accessories and/or disposable objects, for instance disposable surgical sponges, gauzes, and/or absorbent pads. When used in surgery, failure to locate an object or item before closing the patient may require additional surgery, and in some instances may have serious adverse medical consequences. In other medical procedures, such as vaginal childbirth deliveries, failure to remove objects, for instance gauze or absorbent pads, can lead to infections and undesired complications.

Some hospitals have instituted procedures that include checklists or requiring multiple manual counts to be performed to track the use and return of objects or items during surgery. Such a manual approach is inefficient, requiring the time of highly trained personnel, and is prone to error.

Another approach employs wireless transponders that are attached to various objects or items used during surgery, and a wireless interrogation and detection system. Such an approach can employ "dumb" wireless transponders, i.e., wireless communications transponders that do not store and/or transmit any unique identifying information. Dumb wireless transponders have traditionally been employed for electronic article surveillance (EAS) to prevent loss of merchandise at retail locations. Alternatively, such an approach can employ radio frequency identification (RFID) wireless transponders, i.e., wireless communications transponders which do store and return a unique identifier in response to an interrogation signal emitted by an RFID interrogator or RFID reader.

In the approach that employs dumb wireless transponders, an interrogation and detection system includes a transmitter that emits pulsed wireless interrogation signals (e.g., radio or microwave frequency) and a detector for detecting wireless response signals returned by the dumb wireless transponders in response to the emitted interrogation signals. Such an automated system detects the presence or absence of dumb wireless transponders, but typically does not detect any unique identifying information. Since no power is required to operate the dumb wireless transponder, such an approach may have better range or better ability to detect objects or items retained within bodily tissue as compared to RFID wireless transponders communicating in similar ranges of wavelength and levels of power, but cannot uniquely identify the dumb wireless transponders.

In the approach that employs RFID wireless transponders, an interrogator or reader includes a transmitter that emits wireless interrogation signals (e.g., radio or microwave frequency) and a detector for detecting wireless response signals returned by the RFID wireless transponders in response to the emitted interrogation signals. Such an automated system advantageously detects the unique identifiers of the RFID wireless transponders; however since some of the power in the interrogation signal is required to operate the RFID wireless transponder such an approach may have shorter range or less ability to detect objects or items retained within bodily tissue as compared to dumb wireless transponders communicating in similar ranges of wavelength and levels of power.

Commercial implementation of such an automated system requires that the overall system be cost competitive, highly accurate, and easy to use. In particular, false negatives must be avoided to ensure that objects are not mistakenly left in the patient and false positives avoided to ensure valuable time and resources are not spent looking for objects which were not actually retained in the patient. Consequently, a new approach to prevention of foreign object retention in medical procedure environments is highly desirable.

BRIEF SUMMARY

An apparatus for use in clinical environments may be summarized as including a trocar, the trocar having a cannula with a proximal end and a distal end, the cannula which delineates a lumen therethrough that extends from the proximal end to the distal end, with a proximal port at the proximal end which provides access to an interior of the lumen from an exterior of the cannula and with a distal port at the distal end which provides access to the interior of the lumen from the exterior of the cannula; at least one trocar antenna, the at least one trocar antenna physically coupled to the trocar and positioned and oriented to provide wireless communications coverage of at least a portion of an interior of the lumen and any wireless communications transponders that pass through the lumen of the cannula; and at least one indicator communicatively coupleable to receive signals that are representative of wireless communications transponders that pass through the lumen of the cannula, if any, the at least one indicator physically coupled to the trocar and positioned and oriented to provide at least one human-perceptible indication that represents at least one of: a count of a number of the wireless communications transponders that have entered the lumen of the cannula, a count of a number of the wireless communications transponders that have exited the lumen of the cannula, a sum of a number of the wireless communications transponders that have entered the lumen of the cannula and a number of the wireless communications transponders that have exited the lumen of the cannula, or a notification of a discrepancy in a number of the wireless communications transponders that have entered the lumen of the cannula and a number of the wireless communications transponders that have exited the lumen of the cannula.

The apparatus may further include at least one processor, the at least one processor communicatively coupled to the at least one interrogator and to the indicator; and at least one nontransitory processor-readable medium that stores at least one of processor-executable instructions or data, execution of which may cause the at least one processor to itemize each of the wireless communications identification transponders that enters the lumen of the trocar; itemize each of the wireless communications identification transponders that exits the lumen of the trocar; compare the itemization of each of the wireless communications identification transponders that exits the lumen of the trocar with the itemization of each of the wireless communications identification transponders that enters the lumen of the trocar; and transmit a signal to the indicator based at least in part on the comparison of the itemizations, the signal which causes the indicator to provide an alert.

The at least one of processor-executable instructions or data, when executed, may further cause the at least one processor to transmit the signal to the indicator based on a discrepancy between the identities of the wireless transponders identified entering and exiting the cannula.

The at least one of processor-executable instructions or data, when executed, may further cause the at least one processor to transmit the signal to the indicator based on the identities of the wireless transponders identified entering the cannula matches the identities of the wireless transponders identified exiting the cannula. The signal may be comprised of a first signal and a second signal, the first signal which is transmitted based upon discrepancy between the identities of the wireless transponders identified entering and exiting the cannula, the first signal which causes the indicator to emit a light of a first wavelength, and the second signal which is transmitted based upon the identities of the wireless transponders identified entering the cannula matching the identities of the wireless transponders identified exiting the cannula, the second signal which causes the indicator to emit a light of a second wavelength. The identities of the wireless transponders identified entering the cannula may include a number of wireless transponders entering the cannula, and the identities of the wireless transponders identified exiting the cannula may include a number of items exiting the cannula. The signal transmitted to the indicator may include an indicator of a difference between the number of items entering the cannula and the number of items exiting the cannula. The at least one trocar antenna may be communicatively coupled to the interrogator via at least one electrical cable. The at least one trocar antenna may be communicatively detachably coupled to the interrogator via at least one electrical cable and a plug. The cannula of the trocar may shield the at least one trocar antenna from response signals emitted by any wireless communications transponders in the exterior of the cannula.

The trocar antenna may include at least one electrically conductive coil that is concentric with at least one of the proximate or the distal ports of the lumen. The cannula of the trocar may include a metal. The trocar antenna may include an electrically insulative sheath that electrically insulates the trocar antenna from the cannula. The cannula of the trocar may include a plastic. The trocar antenna may be encased in the plastic of the cannula. The at least one trocar antenna may be positioned and oriented to provide coverage of an entirety of the interior of the lumen of the cannula and all wireless communications transponders in the interior of the lumen of the cannula. The at least one trocar antenna may be positioned and oriented to provide coverage of the proximal port and all wireless communications transponders passing through the proximal port. The at least one trocar antenna may be positioned and oriented to provide coverage of the distal port and all wireless communications transponders passing through the distal port. The at least one trocar antenna may include a first trocar antenna positioned and oriented to provide coverage of the proximal port and all wireless communications transponders passing through the proximal port, and at least a second trocar antenna positioned and oriented to provide coverage of the distal port and all wireless communications transponders passing through the distal port. Processor-executable instructions or data, when executed, may cause the at least one processor to itemize each of the wireless communications identification transponders that exits the lumen of the trocar via at least one of the distal port and the proximal port; and itemize each of the wireless communications identification transponders that enters the lumen of the trocar via at least the distal port and the proximal port.

The trocar may further include a seal located at least proximate the proximate end and an obturator that movingly extends through the cannula with a piercing tip located proximate the distal end. The proximal port may be sized and dimensioned to receive pieces of disposable gauze, each piece of disposable gauze tagged with a respective dumb wireless communications transponder that does not store any unique identifier nor provide any unique identifier. The proximal port may be sized and dimensioned to receive pieces of disposable gauze, each piece of disposable gauze tagged with a respective radio frequency identification (RFID) wireless communications identification transponder.

A method of operation of an apparatus, the apparatus which may include a trocar having a cannula with a lumen having a proximal port at a proximal end of the lumen and a distal port at a distal end of the lumen, at least one trocar antenna, at least one indicator located along an exterior of the at least one trocar, and at least one interrogator communicatively coupled to the at least one trocar antenna, may be summarized as including causing, by the interrogator, the at least one trocar antenna to emit at least one interrogation signal having a range that covers at least a portion of an interior of the lumen of the cannula; detecting, by the interrogator, any response signals to the at least one interrogation signal, the response signals returned from any wireless communications identification transponders in the portion of the interior of the lumen of the cannula; identifying, by the interrogator, each of a number of wireless communications identification transponders in the portion of the interior of the lumen of the cannula based on the detected response signals; storing to at least one nontransitory processor-readable medium information that itemizes each of the wireless communications identification transponders that enters the lumen of the trocar, and itemizes each of the wireless communications identification transponders that exits the lumen of the trocar; comparing the itemization of each of the wireless communications identification transponders that exits the lumen of the trocar with the itemization of each of the wireless communications identification transponders that enters the lumen of the trocar; and generating a notification at the indicator based at least in part on the comparison of the itemization.

Itemizing each of the wireless communications identification transponders that enters the lumen of the trocar may further include itemizing each of the communications identification transponders that enters the lumen of the trocar via one of the distal port and the proximal port; and itemizing each of the wireless communications identification transponders that exits the lumen of the trocar further comprises itemizing each of the wireless communications identification transponders that exits the lumen of the trocar via one of the distal port and the proximal port.

The notification may further include causing the notification to be provided in response to a discrepancy in the comparison of the itemization of each of the wireless communications identification transponders that exits the lumen with the itemization of each of the wireless communications identification transponders that enters the lumen of the trocar.

The notification may further include causing the notification to be provided in response to the itemization of each of the wireless communications identification transponders that exits the lumen matching the itemization of each of the wireless communications identification transponders that enters the lumen of the trocar. Generating a notification at the indicator may further include emitting a light of a first wavelength at the indicator in response to the discrepancy in the comparison of the itemization of each of the wireless communications identification transponders that exits the lumen with the itemization of each of the wireless communications identification transponders that enters the lumen of the trocar, and emitting a light of a second wavelength at the indicator in response to the itemization of each of the wireless communications identification transponders that exits the lumen matching the itemization of each of the wireless communications identification transponders that enters the lumen of the trocar.

The method may further include generating a time and date stamp that represents a time and date of the itemization; and storing the generated time and date stamp logically associated with the itemization.

The method may further include determining, by at least one processor, a first count of a total number of items that enter the lumen of the cannula based on the detected response signals; and determining, by the at least one processor, a second count of a total number of items that exit the lumen of the cannula based on the detected response signals.

The method may further include displaying at the indicator a difference between the first count of the total number of items that enter the lumen of the cannula and the second count of the total number of items that exit the lumen of the cannula.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers and/or medical equipment and medical facilities have not been shown or described in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Figure 1A:
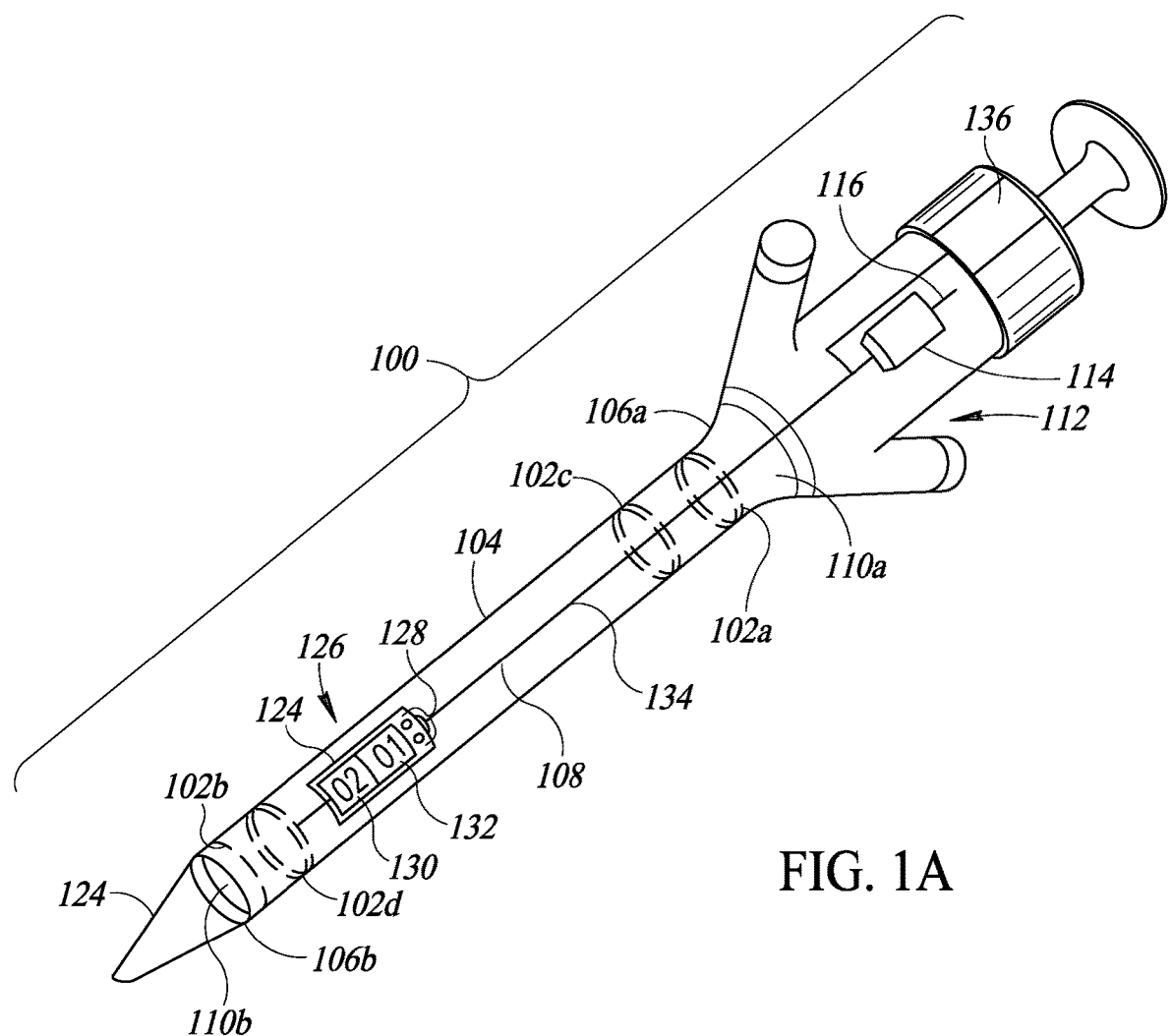
FIG. 1A is an isometric view of a trocar with a number of antennas and an interrogator or reader communicatively coupled to the antennas, according to at least one illustrated implementation.

The headings and Abstract of the Disclosure provided herein are for convenience only and do not interpret the scope or meaning of the embodiments. FIG. 1A shows a trocar 100 with one or more antennas 102a, 102b, 102c, 102d (four shown, collectively 102), according to at least one illustrated implementation.

The trocar 100 can take any of a large variety of forms, resembling or even being identical to existing trocars, with the addition of one or more antennas 102. The trocar 100 typically has a cannula 104 with a first or proximal end 106a and a second or distal end 106b. As used herein, the term "distal" refers to that portion of a device that is farther from the user, while the term "proximal" refers to that portion of a device that is closer to the user. The cannula 104 may be comprised of plastic and/or metal. The cannula 104 delineates a lumen 108 through the cannula 104 that extends from the proximal end 106a to the distal end 106b. A first or proximal port 110a at the proximal end 106a and a second or distal port 110b at the second end 106b provide access to an interior of the lumen 108 from an exterior of the cannula 104 or trocar 100. The trocar 100 typically includes one or more seals 112, for example, at or proximate the proximal end 106a of the cannula 104. The seal(s) 112 allows instruments to pass through the lumen 108 of the cannula 104 while preventing air from escaping from a bodily cavity. The proximal port 110a may be sized and dimensioned to receive pieces of disposable gauze (discussed below) each of which may be tagged with one or more of an RFID wireless communications identification transponder and/or a dumb wireless communications transponder. The trocar 100 typically includes an obturator 124 that movingly extends through the cannula 104. The obturator 124 may, for example, have a piercing tip at or proximate the distal end 106b, that in operation pierces, slices or penetrates bodily tissue (e.g., skin) of a patient and thereby allows the cannula 104 to penetrate bodily tissue.

The at least one trocar is physically coupled to the trocar 100, for example carried by the cannula 104, and positioned and oriented to provide wireless communications coverage of at least a portion of an interior of the lumen 108, including coverage of any wireless communications identification transponders (e.g., RFID transponders and/or dumb wireless transponders) that pass through the lumen 108 of the cannula 104. The at least one trocar antenna 102 can, for example, be physically releasably or removably coupled to the trocar 100. The at least one trocar antenna 102 can, for example, be comprised of at least one electrically conductive coil that is concentric with at least one of the proximate or the distal ports 110a, 110b of the lumen 108. A range of the at least one trocar antenna 102 should encompass the interior of the lumen 108 at least at one cross-section of the lumen 108 taken across the lumen 108, for instance perpendicular to a major, principal or longitudinal axis of the lumen 108. The range can be an emission range, i.e., the effective range of an interrogation signal emitted by the trocar antenna 102. The range can additionally or alternatively be a detection range, i.e., the effective range at which a response signal is detected via the trocar antenna 102.

In some implementations, one or more of the trocar antenna 102 may be positioned and oriented to provide coverage of an entirety of the interior of the lumen 108 of the cannula 104 in order to detect response signals form one or more wireless communications transponders in the interior of the lumen 108 of the cannula 104. In some implementations, one or more of the trocar antennas 102 (e.g., first trocar antenna 102a) be may positioned and oriented to provide coverage of the proximal port 110a and all wireless communications transponders passing through the proximal port 110a. In some implementations, one or more of the trocar antennas 102 (e.g., second trocar antenna 102b) may be positioned and oriented to provide coverage of the distal port 110b and all wireless communications transponders passing through the distal port 110b.

Each trocar antenna 102 comprises at least one electrically conductive coil or band, for example a C-shaped band or an O-shaped band. The band may, for example be resilient, and may be made of metal (e.g., spring steel), or a plastic or other material. One or more additional fasteners (e.g., clamps, screws, nuts, bolts, adhesives) can be employed to secure (e.g., releasably secure) the trocar antenna 102 to the trocar 100. Release, detachment or removal of the trocar antenna 102 from the trocar 100 allows the trocar antenna to be sterilized and reused. In contrast, trocars 100 are often single use disposable items. While sometimes referred to in the singular, some implementations can employ two or more trocar antenna 102. Each trocar antenna 102 may be separately attachable to and detachable from the trocar 100, or may constitute a single integral unit attachable and detachable from the trocar 100.

As illustrated, a first trocar antenna 102a may, for example, be concentric with and located at or proximate the proximal port 110a. As illustrated, a second trocar antenna 102b may be concentric with and located at or proximate the distal port 110b. Thus, the at least one trocar antenna 102 can include a first trocar antenna 102a positioned and oriented to provide coverage of the proximal port 110a and all wireless communications identification transponders passing through the proximal port 110a, and at least a second trocar antenna 102b positioned and oriented to provide coverage of the distal port 110a and all wireless communications identification transponders passing through the distal port 110b. Optionally, a third trocar antenna 102c may, for example, be concentric with and located at or proximate the proximal port 110a spaced longitudinally with respect to the first trocar antenna 102a. Optionally, a fourth trocar antenna 102d may, for example, be concentric with and located at or proximate the distal port 110b, spaced longitudinally with respect to the first trocar antenna 102a. The longitudinal spacing of the trocar antenna 102 may facilitate determination of a direction of travel of an object through the lumen 108 of the cannula 104. For example, detection of successive passage past respective trocar antennas can advantageously indicate whether an object is moving from the proximal end toward the distal end, or conversely from the distal end toward the proximal end. Discrete circuitry and/or a suitably programmed microprocessor in the interrogator 114, or remote from and responsive to output of the interrogator 114, can determine direction, for instance based on timing of a sequence of detection events produced by passage of an object past one or more trocar antennas 102. Alternatively or additionally, the discrete circuitry or programmed microprocessor may determine direction from a frequency of the response signal, for example taking into account a Doppler shift as an object moves relatively towards and away from one or more trocar antennas 102.

An interrogator or reader 114 (e.g., RFID interrogator or reader, dumb wireless transponder interrogator) and associated antenna 116 can be physically coupled to the trocar 100, and communicatively coupled to the trocar antenna(s) 102. Alternatively, the trocar 100 can include one or more transmitters and associated antennas to wirelessly communicatively couple the trocar antenna(s) 102 to an external interrogator or reader (e.g., RFID interrogator or reader, dumb wireless transponder interrogator). Alternatively, the trocar 100 can include one or more electrical cables and connectors (e.g., plug) to detachably communicatively couple the at least one trocar antenna to an external interrogator or reader.

The interrogator or reader 114 can, for example, be physically releasably or removably coupled to the trocar 100, for instance via one or more bands, clamps or other fasteners. Release, detachment or removal of the interrogator or reader 114 from the trocar 100 allows the trocar antenna to be sterilized and reused.

The interrogator or reader 114 is operable to cause the trocar antenna(s) 102 to emit interrogation signals (e.g., radio or microwave frequencies), and to detect response signals from any exposed wireless communications identification transponders that pass through the lumen of the cannula 104, preferably without detecting any wireless communications identification transponders that are outside the interior of the lumen.

In some implementations, the trocar 100 may be a shielded trocar. In particular, the cannula 104 of the trocar 100 may shield the trocar antenna(s) 102 from response signals emitted by any wireless communications identification transponders or other antennas located in externally with respect to the interior of the lumen 108 of the cannula 104 of the trocar 100, as well as from radio frequency or microwave frequency noise in the ambient environment external to the lumen 108 of the cannula 104. For example, the cannula 104 of the trocar 100 may be electrically conductive, for example comprising a metal, for instance stainless steel.

The trocar 100 may include one or more switches or sensors positioned and/or oriented to detect the presence or passage of one or more tagged items, and communicatively coupled to provide a trigger signal to cause the interrogator or reader 114 to cause interrogations signals to be sent. The switch or sensor can take any of a large variety of forms, for example a Reed switch, an optical emitter (e.g., infrared LED) and sensor pair, a mechanical switch, slide switch, push button switch, contact switch, inductive sensor, etc. The switch or sensor can be fixed to the trocar 100, or may be removably or releasably secured thereto via one or more bands, clamps, or other fasteners. Release, detachment or removal of the switch or sensor from the trocar 100 allows the switch or sensor to be sterilized and reused. The switch or sensor employ wired communications or may include a radio (e.g., Bluetooth® radio) to provide for wireless communications.

The trocar 100 may include an indicator 124 that may be used to provide at least one human-perceptible indication 126 associated with the detection of wireless communication transponders (e.g., RFID transponder and/or dumb wireless transponder) that have passed through the interior of the lumen 108. In some implementations, the human perceptible indication 126 may include a set of light sources 128 each one of which may emit a light of a specific wavelength and/or pattern, a count showing the total number of transponders passing through the lumen 108 (e.g., a sum of the number of transponders entering into and exiting from the lumen 108), a count showing the number of transponders that have entered into and/or exited from the lumen 108 in one or more particular directions (e.g., first number 130, second number 132), a haptic response, and/or an audible response (e.g., an audible alarm). Such human perceptible indications 126 may be generated in some implementations to indicate a discrepancy in the number of wireless communications transponders that have entered the lumen 108 of the cannula 104 and a number of the wireless communications transponders that have exited the lumen 108 of the cannula 104.

In some implementations, the indicator 124 may be electrically and/or communicatively coupled to the interrogator 114 via one or more electrical cables 134. In such an implementation, the interrogator 114 may detect response signals at one or more of the trocar antennas 102, and transmit information to the indicator 124 based upon the detected response signals, in which the detected response signals are representative of the wireless communications transponders passing through the lumen 108 of the cannula 104. In such an implementation, the interrogator 114 may identify the trocar antenna 102 that detected the response signals.

In some implementations, a processor 136 may be communicatively coupled to one or more of the trocar antennas 112 and/or the interrogator 114. In some implementations, the processor 136 may be located on the trocar 100. In some implementations, the processor 136 may be located remotely from the interrogator 114. In some implementations, the processor 136 may execute one or more instructions to itemize the each of the RFID transponders that enters and/or exits the lumen 108. In some implementations, the processor 136 may compare the itemized RFID transponders that enter the lumen 108 with the RFID transponders that exit the lumen 108. In such an implementation, the processor 136 may transmit one or more signals to the indicator 124 based upon the comparison. In some implementations, such one or more signals may cause the indicator 124 to emit an alarm when the comparison shows a discrepancy between the itemized RFID transponders that enter the lumen 108 and the RFID transponders that exit the lumen 108.

In some implementations, the processor may identify the RFID transponders that enter the lumen 108 and the RFID transponders that exit the lumen 108. In such an implementation, the processor 136 may compare the identities of the RFID transponders that enter the lumen 108 with the identities of the RFID transponders that exit the lumen 108. In such an implementation, the processor 136 may detect a discrepancy between the RFID transponders that enter the lumen 108 and the identities of the RFID transponders that exit the lumen 108. In such an implementation, the processor 136 may transmit one or more signals to the indicator 124 based upon a detected discrepancy. In such an implementation, the one or more signals received by the indicator 124 may cause the indicator to emit one or more alarms. In some implementations, the alarm may be a visual alarm (a flashing light and/or a light of a first wavelength), an audible alarm, and/or a haptic alarm. In some implementations, the processor 136 may transmit one or more signals to the indicator 124 when the identities of the RFID transponders that enter the lumen 108 match the identities of the RFID transponders that exit the lumen 108. In such an implementation, the one or more signals may cause the indicator 124 to display a light of a second wavelength to indicate that all of the detected items input into the lumen 108 have been removed. In such implementations, the identities of the wireless transponders may correspond to one or more medical items (e.g., gauze or pads).

The indicator 124 may display information based upon the received signal. For example, in some implementations, the indicator 124 may display a first number 130 that corresponds to the number of RFID transponders that enter the lumen 108 (e.g., that travel from the proximal port 110a towards the distal port 110b). The indicator 124 may display a second number 132 that corresponds to the number of RFID transponders that exit the lumen 108 (e.g., that travel from the distal port 110b towards the proximal port 110a). In some implementations (e.g., FIG. 1D), the indicator 124 may have a display that shows a combined number 138. The combined number 138 may indicate a sum of a number of RFID transponders and/or dumb wireless transponders that enter the lumen 108 and a number of RFID transponders and/or dumb wireless transponders that exit the lumen 108. In some implementations, the combined number 138 may indicate a difference between the number of RFID transponders and/or dumb wireless transponders that enter the lumen 108 and the number of RFID transponders and/or dumb wireless transponders that exit the lumen 108.

Figure 1B:
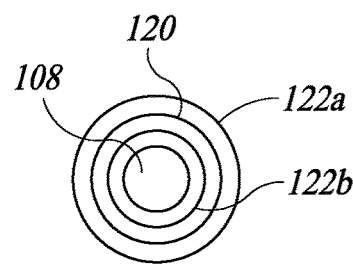
FIG. 1B is a cross-sectional view of a trocar with a number of antennas, according to at least one illustrated implementation.

FIG. 1B shows a portion of a trocar 100a similar to that of FIG. 1A, and including an RF shield 120 encased between two electrically non-conductive layers 122a, 122b, according to at least one illustrated implementation. The RF shield 120 can comprise an electrically conductive material, for example a metal. The RF shield 120 can comprise an electrically conductive sheath, for instance an electrically conductive sheet of material, or an electrically conductive mesh or grid. The two electrically non-conductive layers 122a, 122b can, for example, comprise a plastic. The two electrically non-conductive layers 122a, 122b can each be made of different materials from one another. In some implementations, the two electrically non-conductive layers 122a, 122b may provide an electrically insulative sheath that electrically insulates the trocar antenna(s) 102 from the cannula 104. The trocar antenna(s) 102 (FIG. 1A) can, for example, be encased in the plastic of the cannula 104. The RF shield 120 may be used to shield one or more of the trocar antennas 102 from response signals emitted by any wireless communications transponders in the exterior of the cannula 104.

Figure 1C:
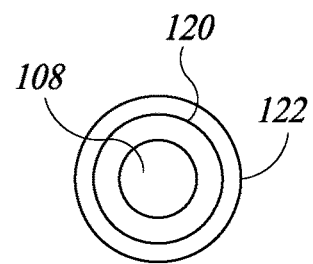
FIG. 1C is a cross-sectional view of a trocar with a number of antennas, according to at least one another illustrated implementation.
Figure 1D:
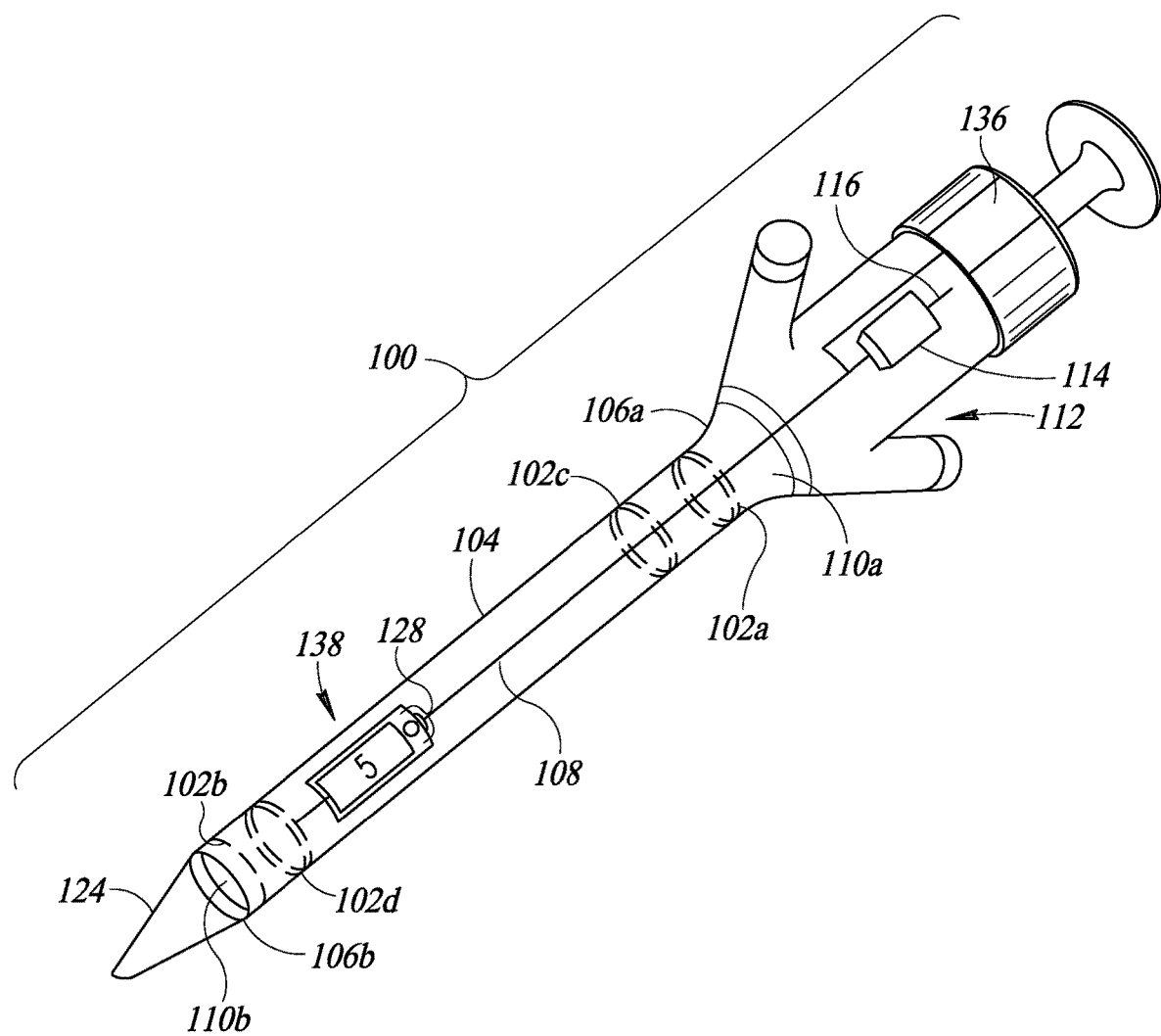
FIG. 1D is an isometric view of a trocar with a number of antennas an interrogator or reader communicatively coupled to the antennas, and an indicator that shows one number, according to at least one illustrated implementation.

FIG. 1C shows a portion of a trocar 100b similar to that of FIG. 1A, and including an RF shield 120 lining an inner wall formed by an outer electrically non-conductive layer 122, according to at least one illustrated implementation.

The RF shield 120 can comprise an electrically conductive material, for example a metal. The RF shield 120 can comprise an electrically conductive sheath, for instance an electrically conductive sheet of material, or an electrically conductive mesh or grid. The electrically non-conductive layer 122 can, for example, comprise a plastic.

Figure 2A:
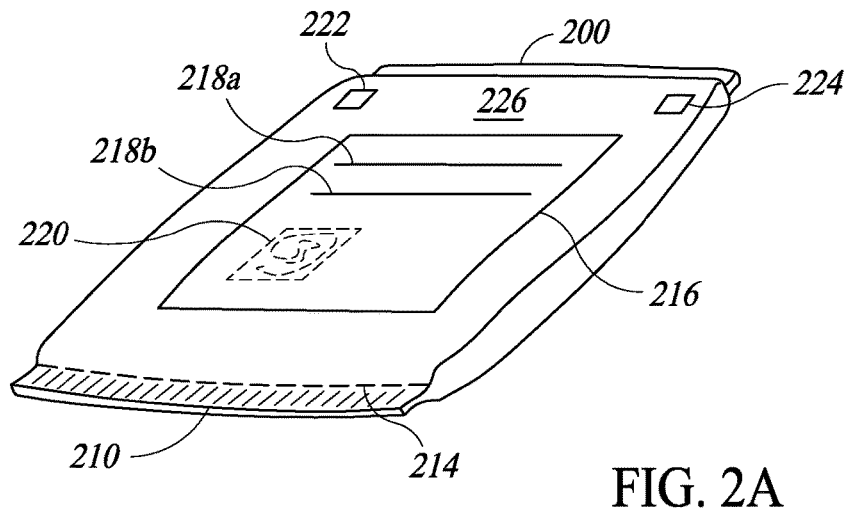
FIG. 2A is an isometric view of a piece of shielded packaging in the form of a shielded envelope or shielded pouch shown in an unopened configuration, the piece of shielded packaging which contains or holds one or more medical or clinical objects or items, each of which includes one or more wireless communications transponders, according to at least one illustrated implementation, the shielded packaging which prevents the wireless communications transponders from receiving interrogations signals and/or responding to interrogations signals at least until the shielded packaging is opened.
Figure 2B:
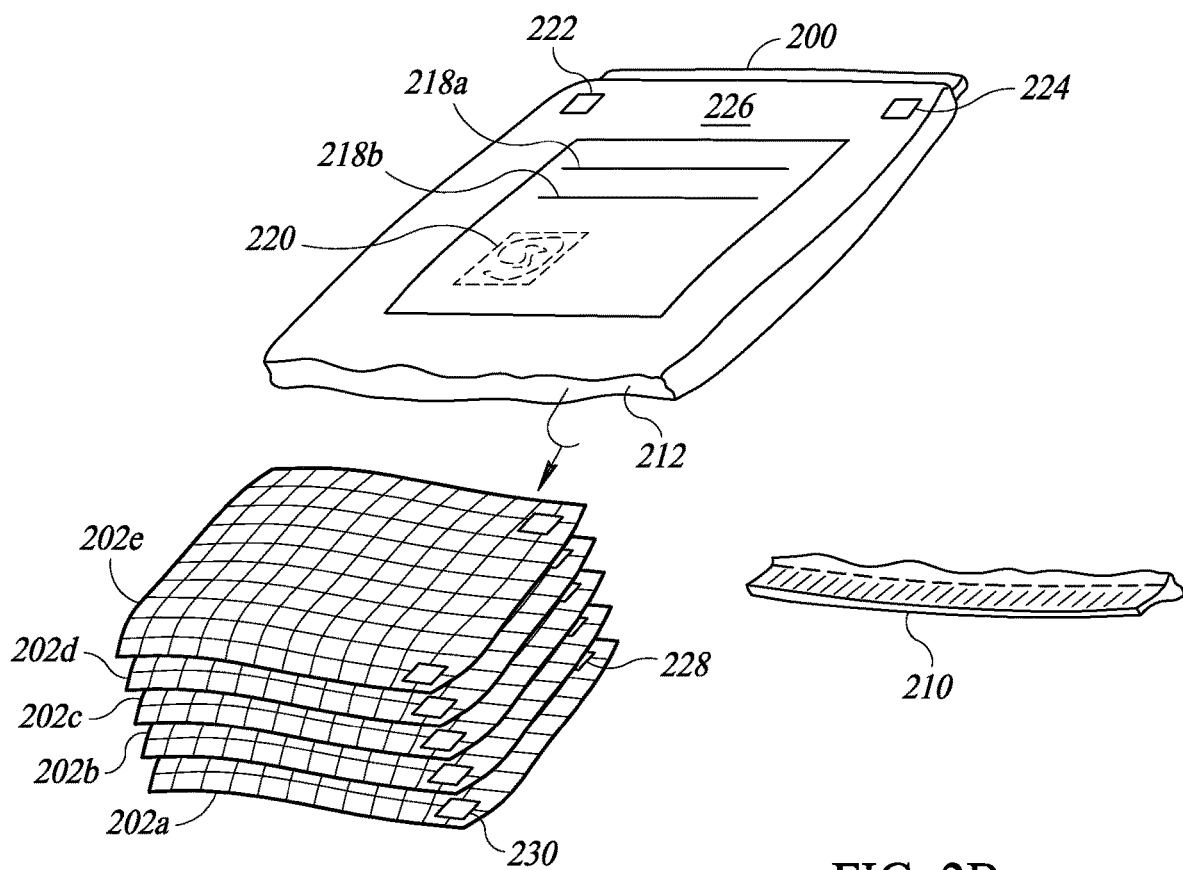
FIG. 2B is an isometric view of the shielded envelope of FIG. 2A shown in an opened configuration, along with a number of medical or clinical objects or items which have been removed from the piece of shielded packaging, and which each includes one or more wireless communications RFID transponders and/or one or more wireless communications dumb transponders, according to at least one illustrated implementation.
Figure 2C:
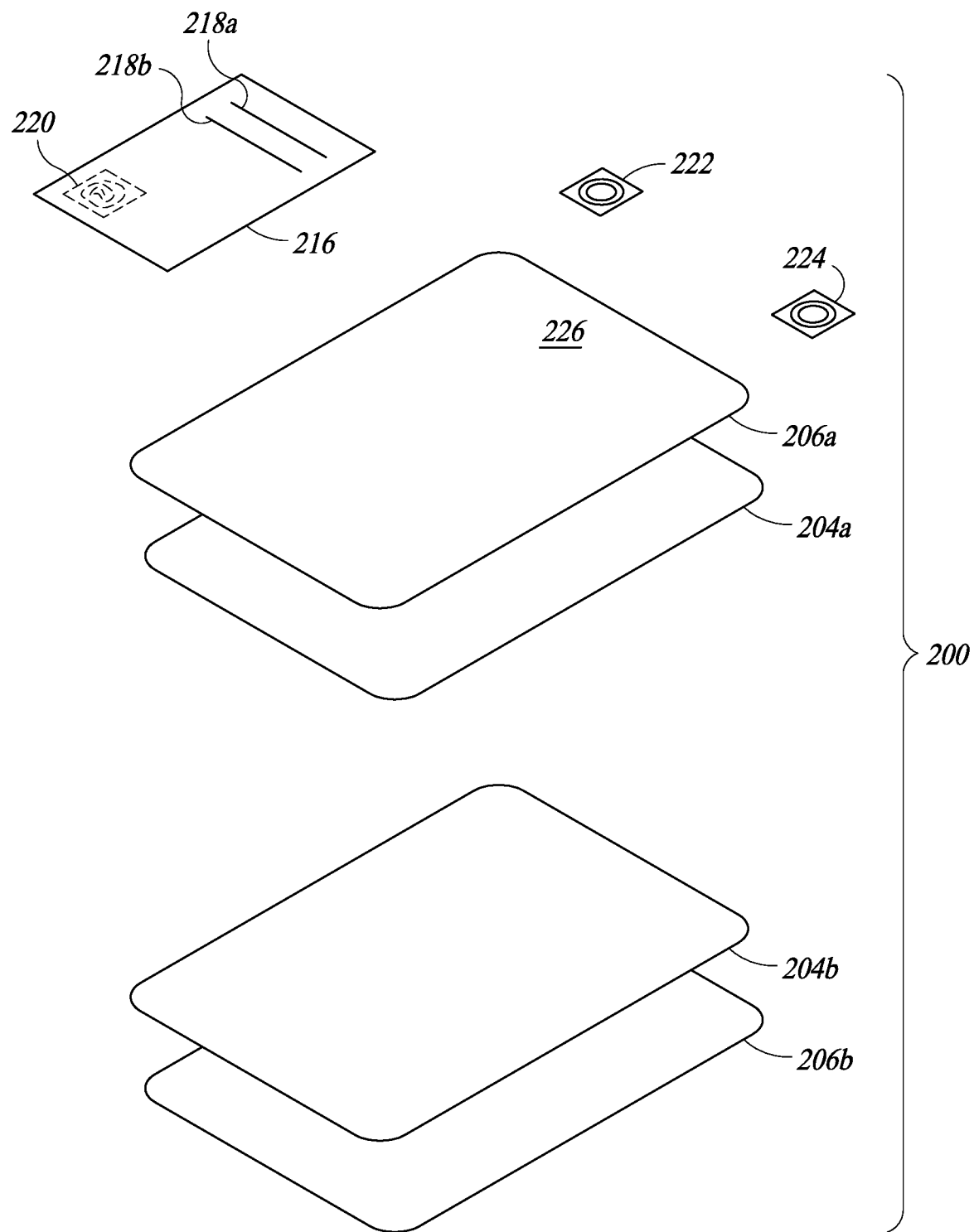
FIG. 2C is an exploded isometric view of the shielded envelope or shielded pouch of FIGS. 2A and 2B, which, according to at least one illustrated implementation, can include a packaging layer, a foil shield layer, and which itself may carry or bear a label with identifying information, and/or one or more wireless communications RFID transponders and/or one or more wireless communications dumb transponders.
Figure 2D:
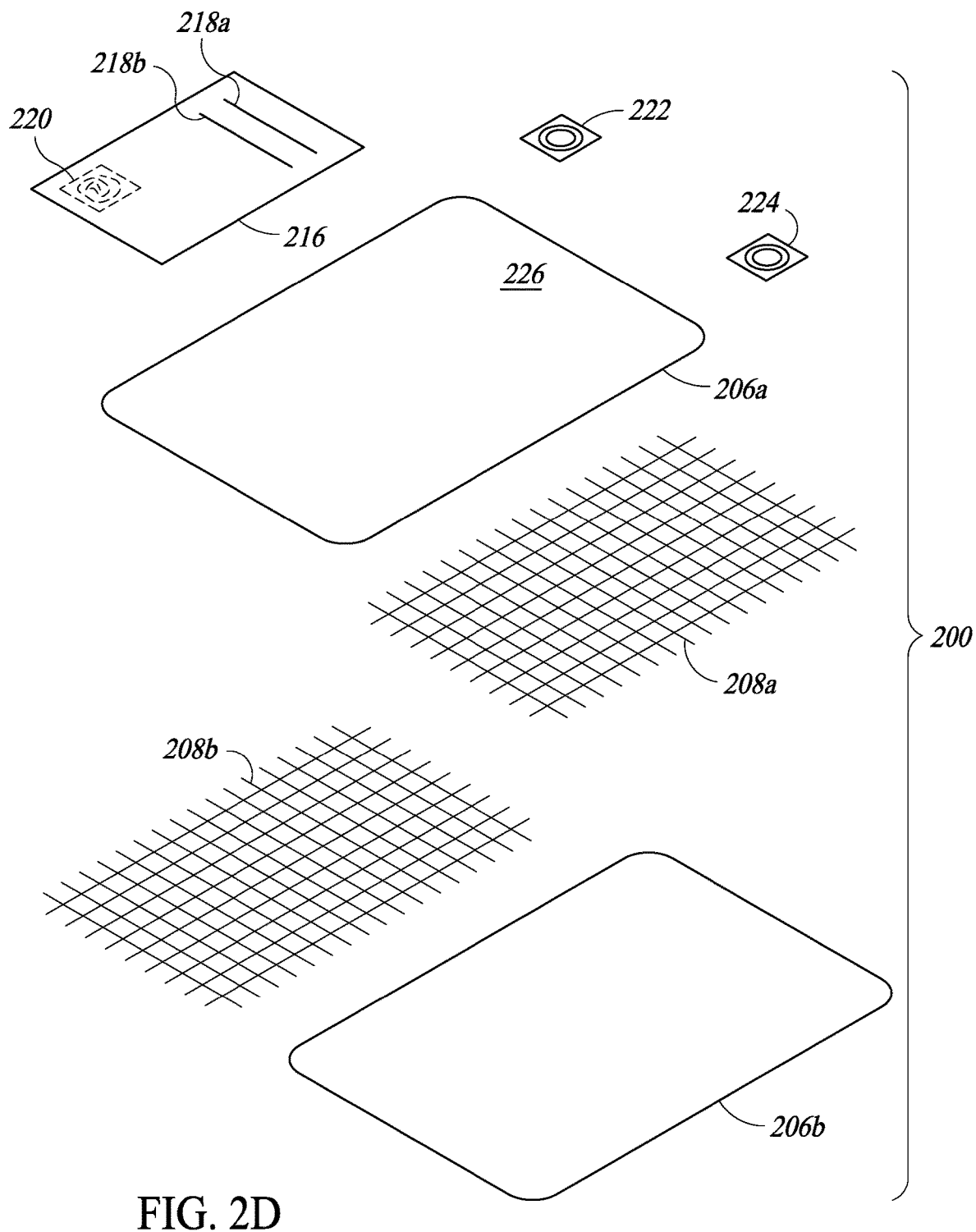
FIG. 2D is an exploded isometric view of the shielded envelope or shielded pouch of FIGS. 2A and 2B, which, according to at least one illustrated implementation, can include a packaging layer, an electrically conductive mesh or grid shield layer, and which itself may carry or bear a label with identifying information, and/or one or more wireless communications RFID transponders and/or one or more wireless communications dumb transponders.

FIG. 2A shows a piece of shielded packaging 200 in a sealed or closed configuration, according to at least one illustrated implementation. FIG. 2B shows the piece of shielded packaging 200 in an unsealed or opened configuration, with the contents of the shielded packaging 200, in the form of surgical sponges, gauze and/or padding 202a-202e (collectively 202, five shown in FIG. 2B), removed from the piece of shielded packaging 200. FIG. 2C shows an exploded view of one implementation of the piece of shielded packaging 200. FIG. 2D shows an exploded view of another implementation of the piece of shielded packaging 200.

The piece of shielded packaging 200 can, as illustrated, take the form of, for example, a packet, envelope or sleeve. The piece of shielded packaging 200 can, for example, take the form of an electrically conductive foil packet, envelope or sleeve that serves as a shield (e.g., Faraday cage) to communications (e.g., radio frequencies, microwave frequencies) for the contents of the shielded packaging 200. The piece of shielded packaging 200 can, for example, comprise aluminum foil, copper foil, or a metalized substrate, for instance a metalized Mylar®, heat-sealable metalized paper polyethylene, heat-sealable metalized plastic laminate, etc. For example, as illustrated in FIG. 2C, the piece of shielded packaging 200 can include a pair of electrically conductive foil layers 204a, 204b laminated to respective non-electrically conductive outer packaging layers 206a, 206b. Alternatively, the shielded packaging 200 may comprise an electrically conductive mesh or grid, which may be laminated to, or sandwiched between electrically non-conductive materials 206a, 206b (e.g., Mylar®, plastic laminate, paper polyethylene, paper). For example, as illustrated in FIG. 2D, the piece of shielded packaging 200 can include a pair of electrically conductive mesh or grid layers 208a, 208b laminated to respective non-electrically conductive outer packaging layers 206a, 206b.

The piece of shielded packaging 200 can, for example, be closed via an adhesive or heat seal 210 along at least one edge. The contents can advantageously be loaded into and sealed in an interior 212 (FIG. 2B) of the piece of shielded packaging 200 in a sterile environment. The piece of shielded packaging 200 may include a slit, notch or tear line 214, that facilitates opening, for example by tearing.

The piece of shielded packaging 200 may bear labeling 216. The label 216 can, for example, include one or more human-readable pieces of information 218a, 218b (e.g., alpha-numeric text or legends). The label 216 can, for example, include one or more optically machine-readable pieces of information, for example one or more machine-readable symbols 220 (e.g., one-dimensional or barcode symbols, two-dimensional or matrix code symbols). The information in the human-readable pieces of information 218a, 218b and/or encoded in the machine-readable symbol(s) 220 can identify the contents of the piece of shielded packaging 200 by name, quantity, manufacturer, and lot and/or batch number.

The piece of shielded packaging 200 may bear one or more wireless communications transponders, for example an RFID transponder 222 and/or a dumb wireless transponder 224. The RFID transponder and/or dumb wireless transponders 222, 224 are preferably located on an exterior 226 of the piece of shielded packaging 200 or at least exterior to a shield layer of the piece of shielded packaging 200. The RFID transponder and/or dumb wireless transponders 222, 224 can be retained via an adhesive or can be heat welded or RF welded to the piece of shielded packaging 200. The RFID transponders 222 can store and return information that identifies the contents of the piece of shielded packaging 200 by name or description (e.g., 4×4 gauze), quantity (e.g., 10 pieces), manufacturer, lot and/or batch number, date of manufacture and/or expiration date.

The contents, for example absorbent surgical sponges, gauze and/or padding 202, may bear one or more wireless communications transponders, for example an RFID transponder 228 (only one called out in FIG. 2B) and/or a dumb wireless transponder 230 (only one called out in FIG. 2B). The RFID transponder and/or dumb wireless transponders 228, 230 can be attached to an exterior surface or an inner surface (e.g., interior folded surface) of the surgical sponges, gauze and/or padding 202. The RFID transponder and/or dumb wireless transponders 228, 230 can be retained via an adhesive, can be heat welded or RF welded to the surgical sponges, gauze and/or padding 202, stitched thereto by cotton or other natural or synthetic thread or fiber, and/or clamped thereto via one or more fasteners (clamp, rivet, snap, staple). The structures and techniques disclosed in U.S. Patent Application Publication No. 2014/0303580, U.S. patent application Ser. No. 15/003,524, and U.S. patent application Ser. No. 15/053,956 may be employed to secure the RFID transponder and/or dumb wireless transponders 222 to the surgical sponges, gauze and/or padding 202. The RFID transponders 228 can store and return information that identifies the contents of the piece of shielded packaging 200 by name, quantity, manufacturer, lot and/or batch number, date of manufacture and/or expiration date.

Such RFID transponders 228 and/or dumb wireless transponders 230 may be detected by one or more of the trocar antenna 102 when the item (e.g., the padding 202) bearing the RFID transponders 228 and/or dumb wireless transponders 230 pass through the interior of the lumen 108. For example, the padding 202 may be introduced to the interior of the lumen 108 via one of the seals 112, and may thereby pass by the first trocar antenna 102a. In this situation, the first trocar antenna 102a may energize one or both of the RFID transponders 228 and/or dumb wireless transponders 230 via an interrogation signal emitted by the first trocar antenna 102a. The RFID transponders 228 and/or dumb wireless transponders 230 may emit a response signal upon being energized, and the response signal may be detected and received by the first trocar antenna 102a at a first point in time.

The padding 202 may continue through the interior of the lumen 108 toward the distal end 106b of the cannula 104. In this situation, the padding 202 may pass by the second trocar antenna 102b, which may energize one or both of the RFID transponders 228 and/or the dumb wireless transponders 230 via an interrogations signal emitted by the second trocar antenna 102b. The RFID transponders 228 and/or dumb wireless transponders 230 may emit a response signal upon being energized, and the response signal may be detected and received by the second trocar antenna 102b at a second point in time that occurs after the first period of time. The direction of travel of the padding 202 from the proximal end 106a towards the distal end 106b of the cannula 104 may be determined based upon a comparison of the first point in time and the second point in time.

The movement of the padding 202 from the distal end 106b towards the proximal end 106a of the cannula 104 may be determined when a response signal from the RFID transponders 228 and/or the dumb wireless transponders 230 is detected at the second trocar antenna 102b at the distal end 106b of the cannula 104 at a first period of time. A response signal from the RFID transponders 228 and/or the dumb wireless transponders 230 may be detected at the first trocar antenna 102a at a second period of time that occurs after the first period of time. The direction of travel of the padding 202 from the distal end 106b towards the proximal end 106a of the cannula 104 may be determined based upon a comparison of the first point in time and the second point in time.

Figure 3A:
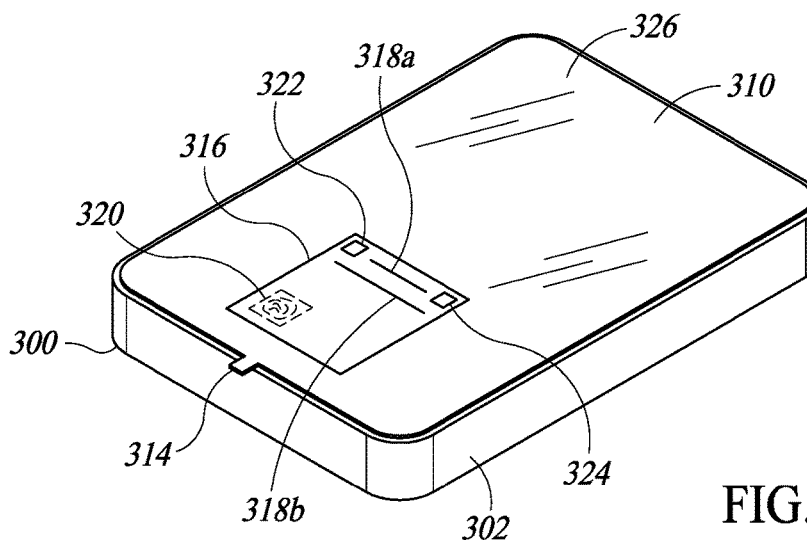
FIG. 3A is an isometric view of the piece of shielded packaging in the form of a shielded tote or tray shown in an unopened configuration, the piece of shielded packaging which contains or holds one or more medical or clinical objects or items, each of which includes one or more wireless communications transponders, according to at least one illustrated implementation, the shielded packaging which prevents the wireless communications transponders from receiving interrogations signals and/or responding to interrogations signals at least until the shielded packaging is opened.
Figure 3B:
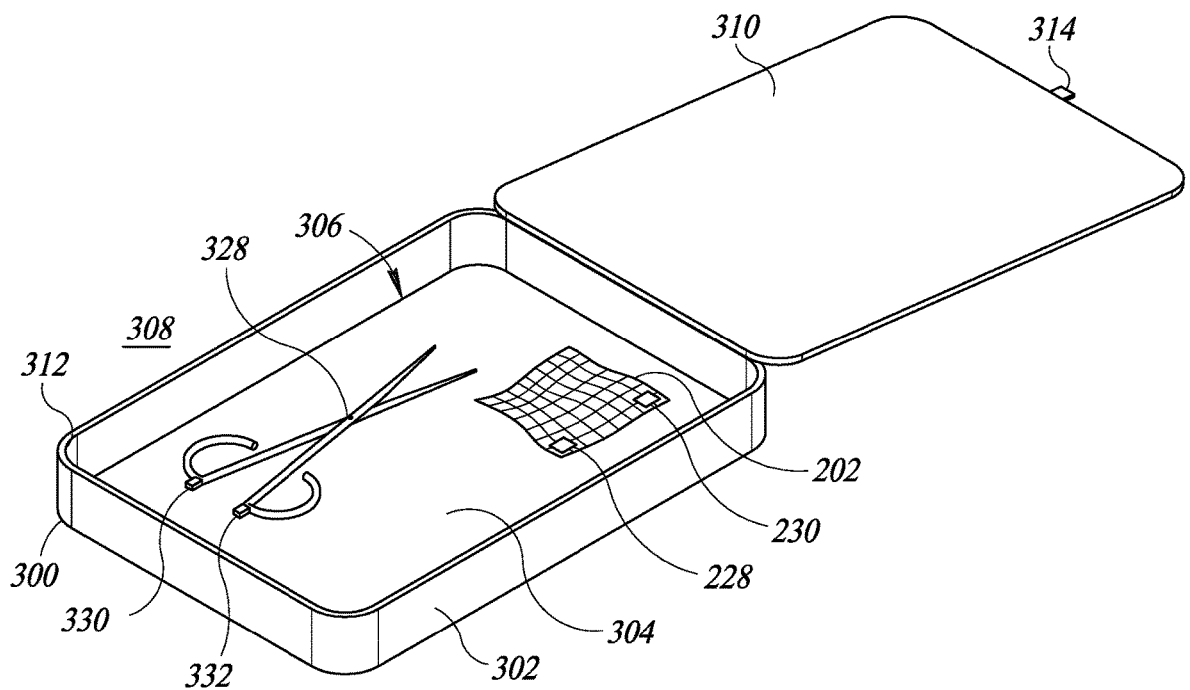
FIG. 3B is an isometric view of the shielded tote or tray of FIG. 3A shown in an opened configuration along with a number of medical or clinical objects or items which have been removed from the piece of shielded packaging, and which each includes one or more wireless communications RFID transponders and/or one or more wireless communications dumb transponders, according to at least one illustrated implementation.

FIG. 3A shows a shielded tote or tray 300 in a sealed or closed configuration, according to at least one illustrated implementation. FIG. 3B shows the shielded tote or tray 300 in an unsealed or opened configuration, according to at least one illustrated implementation. The shielded tote or tray 300 includes body 302 that defines an interior 304 (FIG. 3A) and an opening 306 to selectively provide access to the interior 304 from an exterior 308 of the shielded tote or tray 300. The shielded tote or tray 300 includes a selectively releasable or removable lid or cover 310, which is movable from a sealed or closed configuration (FIG. 3A) to an unsealed or open configuration (FIG. 3B). The lid or cover 310 can, for example, be releasable retained along a lip 312 (FIG. 3B) of the body 302 that surrounds the opening 306, for instance via a pressure sensitive adhesive.

As illustrated in FIGS. 3A and 3B, the body 302 may be formed of an electrically conductive material, for example a metal, for instance stainless steel. The lid or cover 310 can be formed of an electrically conductive material, for example a metal, for instance stainless steel, or more preferably a metal foil (e.g. aluminum foil, copper foil), or a metalized flexible substrate, for instance a metalized Mylar®, metalized paper polyethylene, metalized plastic laminate, cardboard, fiberboard, etc. The combination of the body 302 and the lid or cover 310 shield (e.g., Faraday cage) the contents of the shielded tote or tray 300 when in the sealed or closed configuration. Removal of the lid or cover 310 exposes the contents of the shielded tote or tray 300 to interrogation signals and allows responses to be sent. The contents of the shielded tote or tray 300 may include one or more paddings 202 that may bear one or more of an RFID transponder 228 and/or a dumb wireless transponder 230.

The shielded tote or tray 300 can, for example, be closed via an adhesive or heat sealed along at least one edge. The contents can advantageously be loaded into and sealed in the interior 304 (FIG. 3B) of the shielded tote or tray 300 in a sterile environment. Alternatively, the contents can be sterilized while in the tote or tray 300, for instance after being hermetically seal via exposure to Gamma radiation and/or heat. The shielded tote or tray 300 may include a pull-tab 314, that facilitates opening, for example by releasing the lid or cover from the body.

The shielded tote or tray 300 may bear labeling 316 (FIG. 3A). The label 316 can, for example, include one or more human-readable pieces of information 318a, 318b (e.g., alpha-numeric text or legends). The label 316 can, for example, include one or more optically machine-readable pieces of information, for example one or more machine-readable symbols 320 (e.g., one-dimensional or barcode symbols, two-dimensional or matrix code symbols). The information in the human-readable pieces of information 318a, 318b and/or encoded in the machine-readable symbol(s) 320 can identify the contents of the shielded tote or tray 300 by name, quantity, manufacturer, and lot and/or batch number. The shielded tote or tray 300 may bear one or more wireless communications transponders, for example an RFID transponder 322 and/or a dumb wireless transponder 324. The RFID transponder and/or dumb wireless transponders 322, 324 are preferably located on an exterior 326 of the shielded tote or tray 300. The RFID transponder and/or dumb wireless transponders 322, 324 can be retained via an adhesive or can be heat welded or RF welded to a portion of the shielded tote or tray 300. The RFID transponders 322 can store and return information that identifies the contents of the shielded tote or tray 300 by name or description (e.g., 4×4 gauze), quantity (e.g., 10 pieces), manufacturer, lot and/or batch number, date of manufacture and/or expiration date.

The contents, for example absorbent surgical sponges, gauze and/or padding 202, may bear one or more wireless communications transponders, for example an RFID transponder 228 (only one called out in FIG. 3B) and/or a dumb wireless transponder 230 (only one called out in FIG. 3B). The RFID transponder and/or dumb wireless transponders 228, 230 can be attached to an exterior surface or an inner surface (e.g., interior folded surface) of the surgical sponges, gauze and/or padding 202. The RFID transponder and/or dumb wireless transponders 228, 230 can be retained via an adhesive, can be heat welded or RF welded to the surgical sponges, gauze and/or padding 202, stitched thereto by cotton or other thread or fiber, and/or clamped thereto via one or more fasteners (clamp, rivet, snap, staple). The structures and techniques disclosed in U.S. Patent Application Publication No. 2014/0303580 may be employed to secure the RFID transponder 228 and/or dumb wireless transponders 230 to the surgical sponges, gauze and/or padding 202. The RFID transponders 228 can store and return information that identifies the contents of the shielded tote or tray 300 by name, quantity, manufacturer, lot and/or batch number, date of manufacture and/or expiration date.

The contents, for example instruments 328, may bear one or more wireless communications transponders, for example an RFID transponder 330 (only one called out in FIG. 3B) and/or a dumb wireless transponder 332 (only one called out in FIG. 3B). The RFID transponder and/or dumb wireless transponders 330, 332 can be attached to an exterior surface or an inner surface (e.g., interior folded surface) of the instruments 328. The RFID transponder and/or dumb wireless transponders 330, 332 can be retained via an adhesive, can be a weld to the instruments 328, stitched or tied thereto by thread or wire, and/or clamped thereto via one or more fasteners (clamp, rivet, snap, staple). The structures and techniques disclosed in U.S. Pat. Nos. 7,898,420 and 8,354,931 may be employed to secure the RFID transponder and/or dumb wireless transponders 330, 332 to the instruments 328.

The RFID transponders 228, 330 can store and return information that identifies the particular item (e.g., absorbent surgical sponges, gauze and/or padding 202, instrument 328) to which the RFID transponder 228, 330 is attached. The information can, for example, include a name or description of the item (e.g., 4×4 gauze, forceps), manufacturer, lot and/or batch number, date of manufacture and/or expiration date.

Figure 4:
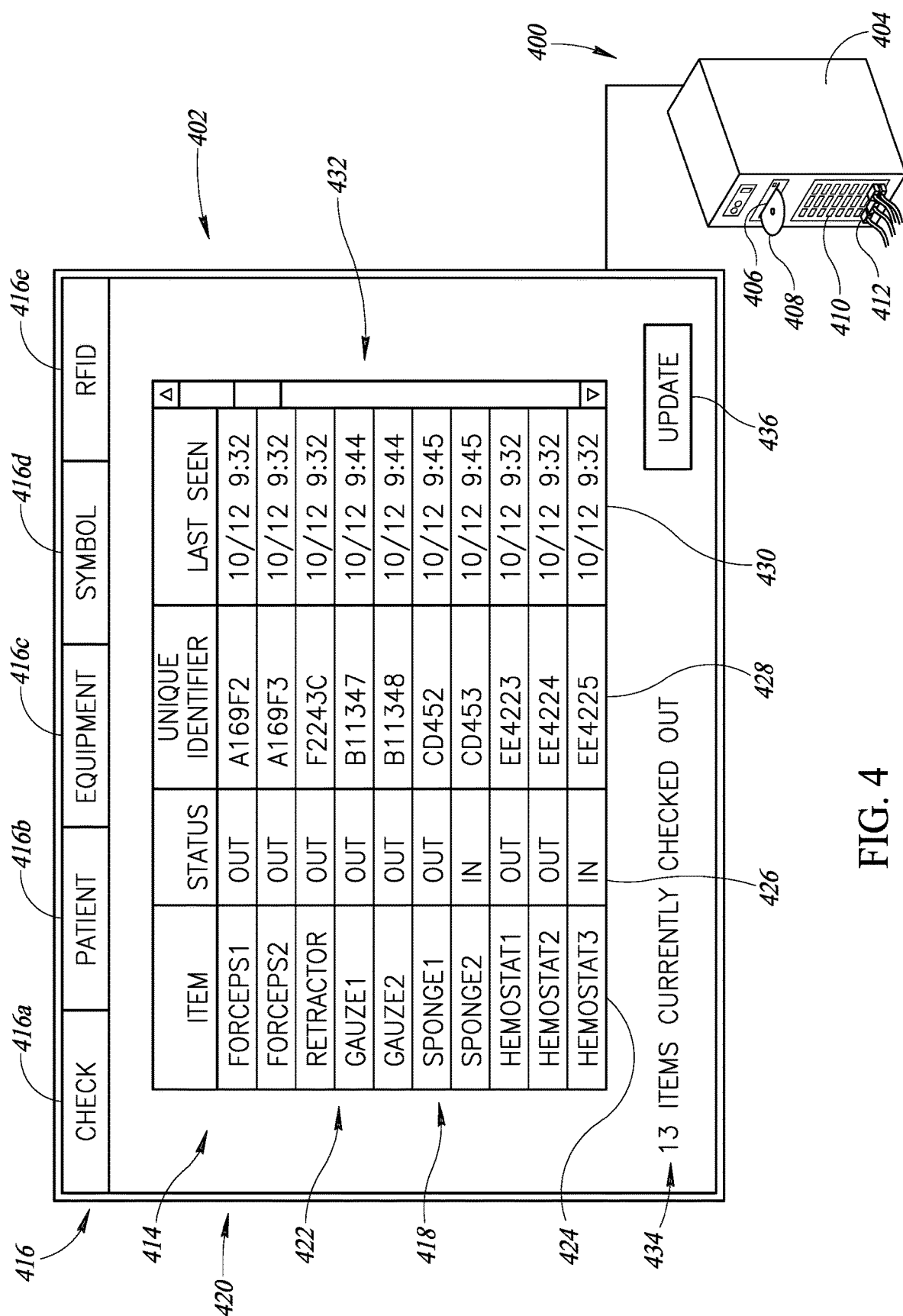
FIG. 4 is a front elevation view of an accounting system and display of the accounting system of FIG. 1, according to one illustrated embodiment.

FIG. 4 shows an accounting system 400 and display 402, according to one illustrated embodiment.

The accounting system 400 may include a housing 404 which houses one or more microprocessors, memory (e.g., RAM, ROM, FLASH), nontransitory computer- or processor-readable storage devices (e.g., hard disk drive, solid state drive), and buses (e.g., power bus, communications buses). The accounting system 400 may include one or more slots 406 or other receptacles to receive computer- or processor-readable media 408, for instance spinning media (e.g., compact disks, DVDs), fixed media (e.g., Flash cards, secure digital (SD) cards, multimedia (MM) cards). The accounting system 400 may also include one or more ports or connectors 410 (only one called out in FIG. 4) to allow selective connection and disconnection of various devices to the control subsystem of the accounting system 400. The connection may provide communications and/or power between the accounting system 400 and various connected devices. Devices may take a variety of forms, for instance one or more radio frequency identification (RFID) interrogation systems, one or more wireless presence/absence interrogation systems, one or more computers or terminals, one or more antennas, and any other device capable of transmitting or receiving data and/or instructions or capable of any other form of communications. Such ports or connectors 410 may take the form of various industry standard ports or connectors, for example Universal Serial Bus ports. While illustrated as physical ports to couple with a connector or plug 412 (only one called out in FIG. 4), the ports 410 may take the form of one or more wireless transmitters, receivers or transceivers. Such may, for instance be compatible with various industry standards, for instance 802.11b, 802.11c, 802.11n, or BLUETOOTH®. Various interfaces may provide access to remote services, such as the Internet or "cloud" storage, or to other computing devices.

The display 402 may be any screen or monitor suitable to display information and/or a user interface (e.g., graphical user interface). The display 402 may, for example take the form of an LCD display panel or a CRT display. The display 402 may be a standalone, separate piece of equipment. Alternatively, the display 402 may be integrated into the housing 404 of the accounting system 400.

The display 402 is communicatively coupled to the processor-based system, discussed below, that may be configured to control the images displayed on the display 402. The display 402 may provide all, or a portion, of a user interface, for an end user to interact with the microprocessors, memory, nontransitory computer- or processor-readable storage devices. The display 402 may take the form of a touch panel display, allowing an end user to enter commands or instructions, or otherwise make selections, via a graphical user interface 414. Alternatively, or additionally, one or more other user input devices may be provided, for instance a keyboard, keypad, mouse, trackball, other pointer control device, or a microphone and voice activated interface.

The graphical user interface 414 may include one or more menus 416. The menus 416 may include icons 416a-416e corresponding to specific functions or operational modes which may be selected. A specific function or mode may be selected by touching the appropriate portion of the user interface or placement of a cursor over the appropriate portion of the user interface. In response, a set of related icons may be displayed for instance by way of a pull-down menu or dialog box. Such may allow further selections or configuration of the specific mode or function. Icons 416a-416e for some exemplary functions or operational modes are illustrated. Selection of a checking function or mode icon 416a causes the accounting system 400 to check medical procedure related instruments and supplies in and out in a database. Selection of a patient function or mode icon 416b may allow patient-specific information to be viewed and/or recorded or modified. Selection of an equipment function or mode icon 416c may allow the end user to read information or data produced or collected by various pieces of medical equipment on the display 402, for instance, blood pressure, heart rate, temperature, blood oxygen levels, respiration, electrocardiogram, etc. The equipment function or mode may additionally, or alternatively, allow an end user to configure parameters of a piece of medical equipment via the user interface. Selection of a symbol reading function or mode icon 416d may allow use of a machine-readable symbol reader (not shown in FIG. 4), while the selection of the RFID reading function or mode icon 416e may allow the use of an RFID interrogator or reader 114 or presence/absence interrogation system(s).

The graphical user interface 414 may have one or more windows or panels 418 (only one illustrated) that present or display information. Multiple windows or panels 418 may be displayed at the same time, or individual windows or panels 418 may be displayed one by one, for example in response to a user selection of a particular function or mode or selection of a particular window or panel 418.

The illustrated window or panel 418 is related to a medical procedure related object accounting mode or function that checks medical procedure related instruments and supplies in and out in a data store (e.g., database) stored in at least one computer- or processor-readable storage medium, hence is also denominated as a checking mode or function.

In the accounting or checking mode or function, the accounting system 400 determines which medical procedure related instruments and supplies are present in at least some portions (e.g., unshielded portions, shielded portions) of medical or clinical environment just prior to or at a start of a medical or clinical procedure. The accounting system 400 also determines which medical procedure related instruments and supplies are present in at least some portions (e.g., unshielded portions, shielded portions) of medical or clinical environment just prior to or at an end a medical or clinical procedure. The accounting system 400 may optionally determine which medical procedure related instruments and supplies are present in at least some portions (e.g., unshielded portions, shielded portions) of medical or clinical environment at intervals during the medical procedure between the start and the end of the medical or clinical procedure, for example from time to time, periodically or even continuously. The accounting system 400 may make such determinations based, for example, on unique identifiers read from one or more RFID transponders 228 by one or more RFID interrogators or readers 114.

As previously noted, the RFID interrogator(s) or reader(s) 114 can transmit interrogation signals from one or more antennas, to excite, power or otherwise cause wireless communications identification or RFID transponders 228 to transmit or emit a response signal. One or more antennas may receive the response signals from the excited or powered RFID transponders 228. The RFID interrogator(s) or reader(s) 114 and/or the accounting system 400 may decode the received response signals to determine identifying information encoded therein. The RFID interrogator(s) or reader(s) 114 and/or the accounting system 400 may logically associate each RFID transponder 228 with an item (e.g., instrument, supply) to which the respective RFID transponder 228 is physically attached.

The accounting system 400 may catalog the medical or clinical procedure related instruments and supplies that are present based on the identifying information. For example, the response signals may contain unique identifiers stored or hardcoded into the RFID transponders 228. These unique identifiers may be mapped to information about the respective instruments and/or supplies, for instance in a data store (e.g., database). Alternatively, information about the respective instruments and/or supplies may be stored in the RFID transponder 228 and encoded in the response signals. Such information may include the name or identity of the instrument or supply, a manufacturer identification, model identification, date put in use, date refurbished or sharpened, date sterilized, method of sterilization, history of use, etc. Such allows tracking and/or tracking of instruments and supplies, before, during and after use.

The accounting system 400 may display information related to the status of the various instruments and/or supplies in a chart 420 or other format. For example, the chart 420 may include an entry, for instance a row 422 (only one called out in FIG. 4), for each instrument and supply present proximate a start of the medical procedure. The instrument or supply may be identified by an identifier 424, for instance a non-unique commonly recognized name or description. A current status of the instrument or supply may be identified by an appropriate status indicator 426 (e.g., In/Out, Present/Absent). Optionally, a unique identifier associated with the instrument or supply may be identified by an appropriate indicator 428 (e.g., unique identifier provided by an RFID transponder 228 physically attached to the instrument or supply). Optionally, "last seen" information identifying a time and date that the instrument or supply was last identified may be provided via an appropriate indicator 430 (e.g., Oct. 12 at 9:32 AM). A scroll bar 432 or similar graphical user interface tool may be provided to allow a user to review information for a large number of instruments and supplies.

The accounting system 400 may determine if there is a discrepancy between the medical or clinical procedure related objects that were present at or proximate a start and at or proximate an end of the medical or clinical procedure. The accounting system 400 may provide a suitable warning or notification 434 if a discrepancy exists, and/or if a discrepancy does not exist. While illustrated as a visual notification, an aural and/or tactile notification may additionally or alternatively be supplied.

The graphical user interface 414 may include one or more icons 436 (only one illustrated), user selection of which may cause certain actions. For instance, selection of an update icon 436 may cause the accounting system 400 to cause a rescan or re-interrogation of the medical or clinical procedure environment, or portions thereof, to account for the presence, absence or location of various medical or clinical procedure related instruments and tools.

Figure 5:
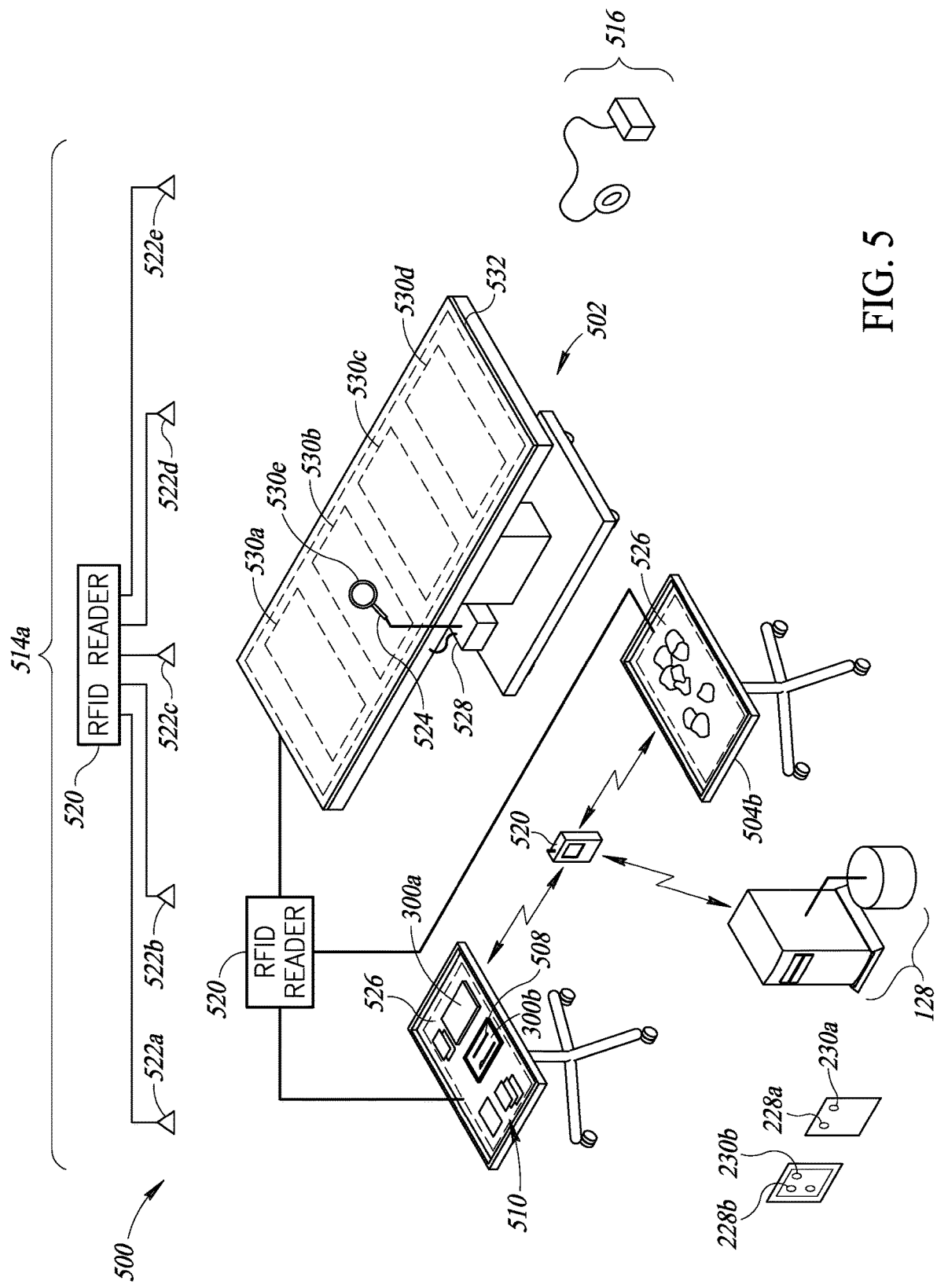
FIG. 5 is an isometric view of a medical or clinical environment in which a medical or clinical procedure is performed, according to one illustrated implementation, and which includes a patient support structure, a number of tables or stands on which medical or clinical procedure instruments and supplies are carried, a number of antennas and one or more radio frequency identification interrogators, a number of antennas and a dumb transponder interrogator, an accounting system communicatively coupled to the interrogators, a number of pieces of medical or clinical procedure objects or items and associated packaging which may advantageously shield the medical or clinical procedure objects or items until opened.

FIG. 5 shows a medical or clinical environment 500 in which a medical or clinical procedures are performed, according to one illustrated implementation. The trocar 100 and/or the gauze or padding 202 may be used within the medical or clinical environment 500.

The medical or clinical procedure environment 500 may take any of a variety of forms, for example a surgical environment or operating room in which surgeries are performed, or an emergency room (ER) in which various medical or clinical procedures are performed. Other medical or clinical procedure environments 500 may take the form of a patient room, examination room or physician's office, etc., in which medical or clinical procedures are performed, or a dedicated labor and delivery (L&D) room in which vaginal child birth or deliveries are performed.

The medical or clinical procedure environment 500 typically includes a patient support structure 502 that can carry a patient (not shown) or portion thereof. The medical procedure environment 500 typically includes a number of accessory tables or stands 504 (two shown in FIG. 5), for example to hold medical or clinical procedure instruments (e.g., the trocar 100) and/or supplies (e.g., gauze or pads 202). The medical or clinical procedure environment 500 may optionally include one or more receptacles (not shown), for example to collect used medical or clinical procedure instruments and/or supplies. The receptacle(s) may advantageously shield (e.g., Faraday cage) the contents of the receptacle(s) from wireless communications (e.g., radio frequencies, microwave frequencies) at least while the receptacle(s) is in a closed configuration.

The medical or clinical procedure environment 500 may include one or more totes or trays 300a, 300b (two shown, collectively 300) that carry instruments and/or supplies. The totes or trays 300 may be hermetically sealed (e.g., tote or tray 300a) until opened (e.g., tote or tray 300b) for use, in order to maintain the contents of the totes or trays 300 sterile prior to introduction of the contents into the medical or clinical procedure environment 500 for use. The totes or trays 300 may advantageously shield (e.g., Faraday cage) the contents of the totes or trays 300 from wireless communications (e.g., radio frequencies, microwave frequencies) at least until the totes or trays 300 are opened and/or the contents removed from the totes or trays 300.

The medical or clinical procedure environment 500 may include one or more pieces of packaging 512a, 512b, 512c (e.g., packets, envelopes or sleeves, three shown, collectively 512) which carry instruments and/or supplies. The packaging 512 may be hermetically sealed (e.g., packets or envelopes 512a, 512b) until opened (e.g., packet or envelope 512c) for use, to maintain the contents of the packaging sterile prior to introduction into the medical or clinical procedure environment 500 for use. The packaging 512 may, for example, take the form of hermetically sealed packets or envelopes 512a, 512b that enclose a number of sponges (e.g., surgical sponges), gauze and/or padding 202. The packaging 512 may advantageously shield (e.g., Faraday cage) the contents of the packaging 512 from wireless communications (e.g., radio frequencies, microwave frequencies) at least until the packaging 512 is opened and/or the contents removed from the packaging 512.

As illustrated and described elsewhere herein, one or more implements or instruments and/or one or more supplies may have one or more wireless communications transponders physically attached thereto. As illustrated and described elsewhere herein, for example one or more trays or totes 300 and/or one or more pieces of packaging 512 may have one or more wireless communications transponders physically attached thereto.

The medical procedure environment 500 may include one or more wireless communications identification interrogation systems, for example one or more radio frequency identification (RFID) interrogation systems 514a. The RFID interrogation system(s) 514a is(are) operable to interrogate wireless communications identification transponders, for example RFID transponders or RFID tags 228a, 228b (only two shown in FIG. 1, collectively 228), receive return signals from RFID transponders or RFID tags 228 which encode unique identifiers, and thereby uniquely identify the RFID transponders or RFID tags 228 within the range of the RFID interrogation system(s) 514a. The RFID transponders or RFID tags 228 store and return unique identifiers (e.g., unique at least within a large enough set to supply a large clinical facility for a month). The RFID transponders or RFID tags 228 may, preferably, take the form of passive RFID transponders or RFID tags which omit batteries and derive power for operation from the interrogation signal. While denominated as "radio frequency," commercial RFID interrogator systems 514a and RFID transponders or tags 228 typically operate or communicate in the low or high frequency (e.g., radio frequency) and/or ultra-high frequency (e.g., microwave frequency) portions of the electromagnetic spectrum. Hence, consistent with common usage in the field of automatic data collection, use of the terms radio frequency and/or RFID is not limited to interrogation systems and wireless communications transponders that employ radio frequency communications, but also include interrogation systems and wireless communications transponders that employ microwave frequency communications.

The medical procedure environment 500 may include one or more wireless communications presence/absence interrogation systems 516. The presence/absence interrogation system(s) 122 is operable to interrogate wireless communications dumb transponders 230a, 230b (only two shown in FIG. 5, collectively 230), receive return wireless communications dumb transponders 230 which do not encode unique identifiers, and determine at least one of a presence or absence of the wireless communications dumb transponders 230 in the range of the wireless communications presence/absence interrogation system(s) 516. The wireless communications dumb transponders 230 are typically simple LC resonant circuits, and do not store, encode or return unique identifiers. The wireless communications presence/absence interrogation system(s) 516 and the wireless communications dumb transponders 230 typically communicate a lower frequency range than RFID interrogator system(s) 514a and the RFID transponders or RFID tags 228. This may advantageously result in better range than obtainable by the RFID interrogator system(s) 514a, and increased ability to detect a wireless communications dumb transponder 230 retained in bodily tissue, even where a patient is obese. In some instances, the frequency range of the RFID interrogator system(s) 514*a* and the wireless communications presence/absence interrogation system(s) 516 does not overlap.

The medical procedure environment 500 may include one or more computers or terminals 518 to allow entry and/or access to information, for example an inventory of instruments and supplies for a particular medical or clinical procedure. The computers or terminals 518 can take a large variety of forms, for example a desktop computer or terminal, laptop computer, netbook computer, tablet computer, or smartphone. The computers or terminals 518 may include a computer housing which houses one or more processors, one or more memories (e.g., RAM, ROM, FLASH), one or more hard disk drives, one or more solid state drives, etc. The computers or terminals 518 may include a display, and one or more user input devices, for example a touch screen or keyboard and/or pointer device such as a computer mouse. For instance, the medical or clinical procedure environment 500 includes a tablet computer to enter and/or provide access to information, for example an inventor of instruments and/or supplies for a given medical or clinical procedure.

The one or more computers or terminals 518 in the medical procedure environment 500 may include an accounting system that is operable to maintain in a nontransitory computer- or processor-readable medium an inventory of instruments and supplies at least for a particular medical or clinical procedure. The RFID interrogation system(s) 514*a* and presence/absence interrogation system(s) 516 are each communicatively coupled to the accounting system via one or more wired or wireless communications channels (e.g., tethered, serial networked). The accounting system can receive information autonomously generated by the RFID interrogation system(s) 514*a* and presence/absence interrogation system(s) 516, allowing automated itemization and inventorying functions to be performed. The computers or terminals 518 may be communicatively coupled to the accounting system via one or more wired or wireless communications channels (e.g., tethered, serial networked) allowing manual entry of information, for instance manual counts of instruments and/or supplies, as well as checking of the status of defined items or of the inventory for a given medical or clinical procedure.

The accounting system may be communicatively coupled to a backend accounting or validation or inventory system (not shown), which stores information in at least one non-transitory computer- or processor-readable medium. The backend accounting or validation or inventory system may be located on the premises of the medical or clinical procedure environment 500, or located remotely therefrom. The backend accounting or validation or inventory system may be communicatively coupled to the accounting system via any variety of wired or wireless communications channels including one or more networks. The backend accounting or validation or inventory system may, for example, manage inventory for multiple medical or clinical procedure environments 500. The accounting system and/or the backend accounting or validation or inventory system may, for example, produce tamper-proof time and date stamps, logically associated with inventory as evidence of counts of instruments and supplies, for instance at the start and at the end of a medical or clinical procedure.

The RFID interrogation system(s) may, for example, include one or more of the trocar RFID interrogation system(s) 100 (FIGS. 1A-1D), which each include one or more antennas 102*a*, 102*b* (FIGS. 1A-1C, two shown, singularly or collectively 102) communicatively coupled to an RFID interrogator or reader 114 (FIG. 1A) to interrogate supplies and/or instruments that pass through a lumen 108 (FIG. 1A) of a trocar 100 (FIG. 1A), for instance as discussed elsewhere herein.

Alternatively or additionally, the RFID interrogation system(s) may, for example, include one or more room-based RFID interrogation system 514*a* that includes one or more RFID interrogators or readers 520 and one or more antennas 522*a*-522*e* (collectively 522) communicatively coupled to the RFID interrogator(s) or reader(s) 520. Commonly available RFID interrogators or readers 520 typically operate in high frequency range (e.g., 13.56 Hz), or ultra-high frequency range (e.g., 433 MHz, 860 MHz to 960 MHz). Other implementations can include a greater or lesser number of RFID interrogators or readers 520 and/or antennas 522. Antennas 522 may be spaced about the medical or clinical environment 500, providing complete or substantially complete (e.g., 85% or greater) coverage of unshielded portions of the medical or clinical environment 500.

Alternatively or additionally, the RFID interrogation system(s) may, for example, include one or more hand-held RFID interrogator 524 to interrogate instruments and/or supplies on the first table or stand 504*a*, and/or on the second table or stand 504*b*, and/or optionally on the patient support surface 502 for instance as discussed elsewhere herein.

Alternatively or additionally, the RFID interrogation system(s) may, for example, include one or more drapes or mats 526, which each include one or more antennas, communicatively coupled to an RFID interrogator or reader to interrogate instruments and/or supplies on the first table or stand 504*a*, and/or on the second table or stand 504*b*, and/or optionally on the patient support surface 502, for instance as discussed elsewhere herein.

The presence/absence interrogation system(s) 516 includes one or more presence/absence interrogators or readers 528 and one or more antennas 530*a*-530*e* communicatively coupled to the presence/absence interrogator(s) or reader(s) 528. The presence/absence interrogators or readers 528 may operate in the frequency range extending, for example, from about 137 kHz to about 160 kHz. Some of the antennas 530*a*-530*d* may be located in a drape, mattress or pad 532 used on the patient support surface 502, providing complete or substantially complete coverage of a patient's body or sterile volume. One or more antennas 530*e* may be hand-held, for example incorporated as part of a wand. The handheld antenna 530*e* is communicatively coupled to the presence/absence interrogator(s) or reader(s) 528 by a wired or wireless communications path, for example via a coaxial cable or other communication path. The drape, mattress or pad 532 used on the patient support surface 502 may employ the structures and methods disclosed in U.S. Pat. No. 9,136,597. The presence/absence interrogation system(s) 516 may, for example, employ the structures and algorithms disclosed in U.S. Patent Application Publication No. 2011/0004276 and U.S. Patent Application Publication No. 2015/0272688.

Figure 6:
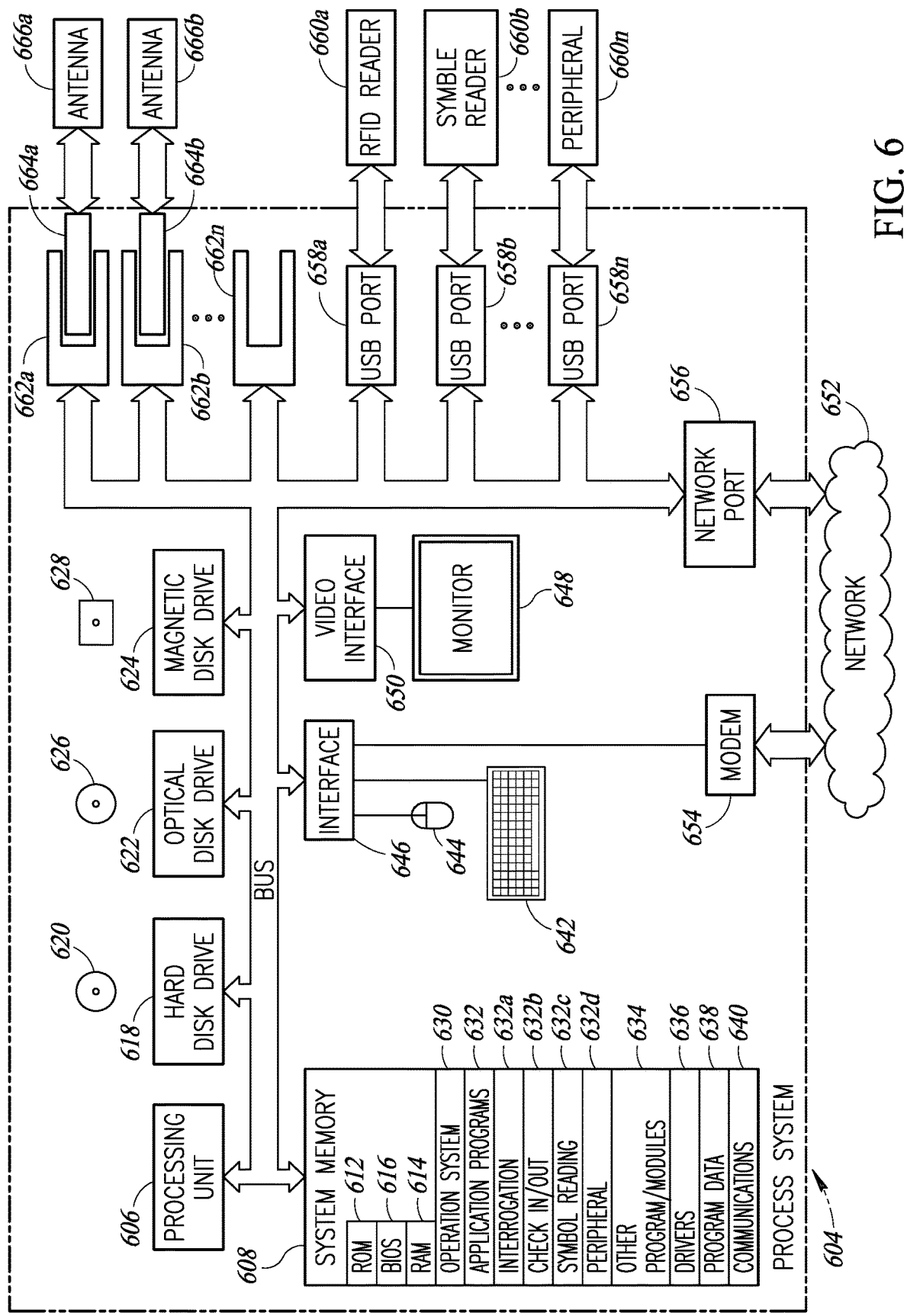
FIG. 6 is a schematic diagram of a control subsystem according to one illustrated embodiment, the control subsystem including a processor system, plug-in boards and various ports to provide communications with antennas, readers and various non-reader peripheral devices or equipment.

FIG. 6 and the following discussion provide a brief, general description of a suitable processor system 604 in which the various illustrated embodiments, as well as other embodiments can be implemented. The processor system 604 can for example implement the wireless presence/absence interrogation systems 516 (FIG. 5). Additionally, or alternatively, processor system 604 can for example implement the accounting system. Although not required, some portion of the embodiments will be described in the general context of computer-executable instructions or logic, such as program application modules, objects, functions, procedures or macros being executed by a computer or processor. Those skilled in the relevant art will appreciate that the illustrated embodiments as well as other embodiments can be practiced with other computer- or processor-based system configurations, including handheld devices, multiprocessor systems, microprocessor-based or programmable consumer electronics, personal computers ("PCs"), network PCs, minicomputers, mainframe computers, and the like. The embodiments can be practiced in distributed computing environments where tasks or modules are performed by remote processor-based devices, which are linked through a communications network. In a distributed computing environment, program modules may be located in local and/or remote memory storage devices, for instance in the cloud. Network connections allow for cloud computing and/or cloud storage.

The processor system 604 may take the form of a conventional personnel computer (PC), which includes one or more processors 606, system memories 608 and system buses 610 that couple various system components including the system memory 608 to the processor 606. The processor system 604 and its components will at times be referred to in the singular herein, but this is not intended to limit the embodiments to a single system or single components, since in certain embodiments, there will be more than one system or other local or remote networked computing device or multiple instances of any component involved. Unless described otherwise, the construction and operation of the various blocks shown in FIG. 6 are of conventional design. As a result, such blocks need not be described in further detail herein, as they will be understood by those skilled in the relevant art.

The processor 606 may be any logic processor, such as one or more central processor units (CPUs), microprocessors, digital signal processors (DSPs), application-specific integrated circuits (ASICs), field programmable gate arrays (FPGAs), etc.

As described in applicant's prior applications, the processor 606 may take the form of a soft processor core, such as that supplied by XILINX under the name MICROBLAZE™, which implements a 32-bit processor including memory caches and a floating point unit. A soft core processor is one that is implemented by interconnected FPGA logic cells instead of by a traditional processor logic. The processor core may be connected to the internal FPGA peripherals using a 32-bit processor bus called the On-Chip Peripheral Bus. The XILINX supplied peripherals for the MICROBLAZE™ processor core include external memory interfaces, timers, and general purpose I/O. Custom logic to create the transmit signals, sample the ADC, and accumulate the transponder return signals may be designed as a peripheral to the soft processor core. The custom logic may be part of the design of the FPGA.

Alternatively, the processor 606 may take the form of a full microprocessor. Non-limiting examples of commercially available microprocessors include, but are not limited to, an 80x86 or Pentium series microprocessor from Intel Corporation, U.S.A., a PowerPC microprocessor from IBM, a Sparc microprocessor from Sun Microsystems, Inc., a PA-RISC series microprocessor from Hewlett-Packard Company, or a 68xxx series microprocessor from Motorola Corporation. For example, the processor 606 may take the form of a full microprocessor such as the ATOM™ processor, commercially available from Intel Corporation. The full microprocessor may be communicatively coupled to multiple analog antenna channels, for example via one or more plug-in boards 664a, 664b (collectively 664, only two shown) which carry respective FPGAs and one or more suitable buses. The FPGA may, for example, act as a co-processor and/or cache. For example, the plug-in boards 664 may implement or carry the circuits disclosed in U.S. patent application Ser. No. 11/759,141 filed Jun. 6, 2007, U.S. Provisional Patent Application Ser. No. 61/056,787 filed May 28, 2008, and U.S. Provisional Patent Application Ser. No. 61/091,667 filed Aug. 25, 2008, with or without change, which Patent Applications are incorporated herein by reference in their entirety.

The system bus 610 can employ any known bus structures or architectures, including a memory bus with memory controller, a peripheral bus, and a local bus. A relatively high bandwidth bus architecture may be employed. For example, a PCI Express™ or PCIe™ bus architecture may be employed, rather than an ISA bus architecture. Suitable FPGAs may include those from ATMEL Corporation. Such FPGAs may advantageously have built in PCIe bus architecture, allowing easy integration. This approach may enable more I/O ports, such as USB ports, may provide more or better video options, and may provide faster data rates from the analog antenna channels than otherwise possible using the ISA bus architecture and a soft processor core approach. Some embodiments may employ separate buses for data, instructions and power.

The system memory 608 includes read-only memory ("ROM") 612 and random access memory ("RAM") 614. A basic input/output system ("BIOS") 616, which can form part of the ROM 612, contains basic routines that help transfer information between elements within the processor system 604, such as during start-up.

The processor system 604 also includes a hard disk drive 618 for reading from and writing to a magnetic hard disk 620, an optical disk drive 622 for reading from and writing to removable optical disks 626, and a removable disk drive 624 for reading from and writing to removable disks 628. The optical disk 626 can be a CD or a DVD, etc., while the removable magnetic disk 620 can be a magnetic floppy disk or diskette. The hard disk drive 618, optical disk drive 622 and removable disk drive 624 communicate with the processor 606 via the system bus 610. The hard disk drive 618, optical disk drive 622 and removable disk drive 624 may include interfaces or controllers (not shown) coupled between such drives and the system bus 610, as is known by those skilled in the relevant art. Additionally or alternatively, the processor system 604 may include one or more solid state drives (SSD). The drives 618, 622, 624, and their associated computer-readable media 620, 626, 628, provide nonvolatile storage of computer-readable instructions, data structures, program modules and other data for the processor system 604. Although the depicted processor system 604 employs hard disk 620, optical disk 626 and removable disk 628, those skilled in the relevant art will appreciate that other types of computer-readable media that can store data accessible by a computer may be employed, such as magnetic cassettes, flash memory cards, Bernoulli cartridges, RAMs, ROMs, smart cards, etc.

Program modules can be stored in the system memory 608, such as an operating system 630, one or more application programs 632, other programs or modules 634, drivers 636 and program data 638.

The application programs 632 may, for example, include interrogation logic 632a, check in/out logic 632b, and machine-readable symbol reading logic 632c, as well as another other peripheral logic 632d associated with operating a non-reader device, referred to in FIG. 6 and elsewhere herein as peripheral logic and peripheral device, respectively. The logic 632a-632d may, for example, be stored as one or more executable instructions. The interrogation logic 632a may include logic or instructions to cause trocar antenna(s) 102 (FIG. 1) and/or RFID interrogator(s) 114 (FIG. 1) to transmit wireless interrogation signals, receive response signals to the interrogations signals, and in the case of RFID transponders decode information encoded in the response signals, for instance unique identifiers stored in RFID transponders. Such may encode information in the interrogation signals, for instance information to be encoded in an RFID transponder. The check in/out logic 632b may include logic to monitor or track a status of various medical procedure instruments and supplies. Such may, for example, update information in a data store (e.g., database) stored on one or more computer- or processor-readable storage media. Such may also allow the generation of queries and retrieval of information from such data store. Such may, for example, update create a record or field in the database for each medical procedure instrument or supply that is present in at least unshielded portions of the medical or clinical environment 500 (FIG. 5) before or at the start of a medical procedure. Such may also, for example, update a respective record or field of the data store or database if a medical procedure instrument or supply is removed from at least unshielded portions of the medical or clinical environment 500 (FIG. 5). Such may also, for example, update a respective record or field of the data store or database if the medical instrument or supply reappears in at least unshielded portions of the medical or clinical environment 500 (FIG. 5) during the medical or clinical procedures.

Such may take the form of identifying a particular instrument as being checked in if detected in at least unshielded portions of the medical or clinical environment 500 (FIG. 5), and otherwise identifying the particular instrument as checked out. A query may be run, either from time to time or before ending a medical or clinical procedure, to ensure that all the medical or clinical instruments and supplies present at the start of the medical or clinical procedure are present and accounted for at the end of the medical procedure. In some implementations, all instruments and supplies are placed in shielded portions (e.g., shielded receptacles) at or proximate the end of the medical or clinical procedure, and the medical or clinical environment is interrogated to determine that no response signals are received. This ensures that no medical instruments or supplies are left behind in a body of a patient undergoing a medical or clinical procedure.

The machine-readable symbol reading logic 632c may allow the capture and decoding of information encoded in machine-readable symbols, such as barcode symbols, area or matrix code symbols and/or stacked code symbols. Such logic is commonly found in dedicated machine-readable symbol readers. The peripheral logic 632d can be any logic loaded into or otherwise stored in a computer- or processor-readable storage medium. The peripheral logic 632d allows operation of a peripheral device, such as a non-reader type device. For instance, the peripheral logic 632d may collect data from one or more pieces of medical procedure equipment (e.g., cautery equipment, heart-lung machine, ablation system, anesthesia deliver apparatus) or medical procedure sensors (e.g., electrode, pulse-oximetry sensor, blood pressure sensor, temperature probe, heart monitor), or other data collection devices. Interrogation logic 632a, machine-readable symbol reading logic 632c, and/or peripheral logic 632d may be automatically loaded into one or more computer- or processor-readable storage medium in response to the communicative coupling of a respective device to a presence/absence interrogator or reader 660a, 660b. Such may advantageously provide plug and play functionality for a wide variety of devices.

The system memory 608 may also include communications programs 640, for example a server and/or a Web client or browser for permitting the processor system 604 to access and exchange data with other systems such as user computing systems, Web sites on the Internet, corporate intranets, extranets, or other networks as described below. The communications programs 640 in the depicted embodiment is markup language based, such as Hypertext Markup Language (HTML), Extensible Markup Language (XML) or Wireless Markup Language (WML), and operates with markup languages that use syntactically delimited characters added to the data of a document to represent the structure of the document or to format information. A number of servers and/or Web clients or browsers are commercially available such as those from Mozilla Corporation of California and Microsoft of Washington.

While shown in FIG. 6 as being stored in the system memory 608, the operating system 630, application programs 632, other programs/modules 634, drivers 636, program data 638 and server and/or browser 640 can be stored on the hard disk 620 of the hard disk drive 618, the optical disk 626 of the optical disk drive 622 and/or the magnetic disk 628 of the magnetic disk drive 620. A user can enter commands and information into the processor system 604 through input devices such as a touch screen or keyboard 642 and/or a pointing device such as a mouse 644. Other input devices can include a microphone, joystick, game pad, tablet, scanner, biometric scanning device, etc. These and other input devices are connected to the processor 606 through an interface 646 such as a universal serial bus ("USB") interface, Firewire, and/or optical Firewire interface, that couples to the system bus 610, although other interfaces such as a parallel port, a game port or a wireless interface or a serial port may be used. A monitor 648 or other display device is coupled to the system bus 610 via a video interface 650, such as a video adapter. Although not shown, the processor system 604 can include other output devices, such as speakers, printers, etc.

The processor system 604 operates in a networked environment using one or more of the logical connections to communicate with one or more remote computers, servers and/or devices via one or more communications channels, for example, one or more networks 652. These logical connections may facilitate any known method of permitting computers to communicate, such as through one or more LANs and/or WANs, such as the Internet, intranet, cloud, and/or extranet. Such networking environments are well known in wired and wireless enterprise-wide computer networks, intranets, extranets, and the Internet. Other embodiments include other types of communication networks including telecommunications networks, cellular networks, paging networks, and other mobile networks.

When used in a WAN networking environment, the processor system 604 may include a modem or wireless hotspot 654 for establishing communications over a WAN, for instance the Internet. The modem 654 is shown in FIG. 6 as communicatively linked between the interface 646 and the network 652. Additionally or alternatively, another device, such as a network port 656, that is communicatively linked to the system bus 610, may be used for establishing communications over the network 652.

One or more interfaces or ports 658a-658n (collectively 658, only three illustrated) that are communicatively linked to the system bus 610, may be used for establishing communications over a WAN, LAN, parallel or serial cable, AC wiring (e.g., ZigBee® protocol transceiver), or wirelessly (e.g., WI-FI® radio, Bluetooth® radio). In some embodiments, the interfaces or ports 658 may take the form of USB ports allowing communication via respective USB cables. Such may allow a variety of equipment to communicate with the processor system 604. For example, such may allow communicative coupling with one or more RFID interrogators or readers 660a, machine-readable symbol readers 660b (e.g., machine-readable symbol scanners or imagers), and peripheral equipment 660n (collectively 660, only three illustrated). The readers 660a, 660b may be configured to transmit pre-processed information to the processor system 604, for instance identifiers read from RFID transponders or optical symbols (e.g., printed or inscribed markings). The processor system 604 may be configured to use such information. For instance, the processor system 604 may be configured to check medical procedure instruments and supplies in and out in the database based on identifiers reader by the readers 660a, 660b. Additionally, or alternatively, the processor system 604 may be configured to control or otherwise send instructions and/or data to the readers 660a. 660b. Likewise, the processor system 604 may be configured to check medical procedure instruments and supplies in and out in the database based on information received from the peripheral equipment 660c. Additionally, or alternatively, the processor system 604 may be configured to control or otherwise send instructions and/or data to the peripheral equipment 660c.

One or more interfaces or slot connectors 662a-662n (collectively 662, only three illustrated) may allow the communicative coupling of plug-in boards 664a, 664b (collectively 664, only two illustrated) to the processor system 604. There may, for example, be one plug-in board 664 for each antenna 666a, 666b (collectively 666, only two illustrated, each of the antennas 666 and plug-in boards 664 constituting a separate channel. The slot connectors 662 may allow expansion or use with different antenna configurations. The plug-in boards 664 may each carry one or more circuits (e.g., analog and/or digital circuit components) configured to transmit interrogation signals from the respective antenna 666 and to monitor the antenna 666 for responses to the interrogation signals. For example, the plug-in boards 664 may implement or carry the circuits disclosed in U.S. patent application Ser. No. 11/759,141 filed Jun. 6, 2007, U.S. Provisional Patent Application Ser. No. 61/056,787 filed May 28, 2008, and U.S. Provisional Patent Application Ser. No. 61/091,667 filed Aug. 25, 2008, with or without change, which Patent Applications are incorporated herein by reference in their entirety. Processor system 604 may automatically recognize and be configured in response to a plug-in board 664 being coupled to an interface or slot connector 662, for example in a fashion similar to the coupling of a USB device to a computer system.

The processor system 604 may include one or more synchronization circuits or logic (not shown) configured to control and synchronize the operation of the various plug-in boards 664. The synchronization circuit or logic may be configured to cause one of the plug-in boards 664 to transmit an interrogation signal from a first antenna, and cause one or more of the other plug-in boards 664 to monitor for a response by a transponder to the interrogation signal. For instance, the synchronization circuit or logic may cause the plug-in boards 664 to monitor all of the antennas 666 for a response to the interrogation signal. Alternatively, the synchronization circuit or logic may cause the plug-in boards 664 to have all of the antennas 666 other than the antenna that transmitted a most recent interrogation signal monitor for a response. Such may advantageously allow monitoring sooner than would otherwise be possible since such can avoid the need to allow the transmitting antenna to return to a quiescent state after transmitting before monitoring for a response. The synchronization circuit or logic may synchronize the plug-in boards 664 to successively cause the various antennas to transmit, for example starting with an antenna at one end, and successively transmitting from each of the antennas in a defined order. As a further alternative, the synchronization circuit or logic may synchronize the plug-in boards 664 to cause the transmission of interrogations signals from a subset of the total set of antennas. While illustrated as removably coupled to the processor system 604, the plug-in boards 664 could be an integral unitary part thereof. For example, the various antennas may be controlled by respective circuits integrated into a signal circuit board. Alternatively, the various antennas may be controlled by a single circuit. While sequential interrogation is described, some implementations may employ parallel interrogation. Whether sequential or parallel interrogation is employed, the processor system 604 may employ serial or parallel processing of information.

In a networked environment, program modules, application programs, or data, or portions thereof, can be stored in a server computing system (not shown) or in the cloud. Those skilled in the relevant art will recognize that the network connections shown in FIG. 6 are only some examples of ways of establishing communications between computers, and other connections may be used, including wirelessly.

For convenience, the processor 606, system memory 608, network port 656, interface 646, interfaces or ports 658 and connector slots 662 are illustrated as communicatively coupled to each other via the system bus 610, thereby providing connectivity between the above-described components. In alternative embodiments of the processor system 604, the above-described components may be communicatively coupled in a different manner than illustrated in FIG. 6. For example, one or more of the above-described components may be directly coupled to other components, or may be coupled to each other, via intermediary components (not shown). In some embodiments, system bus 610 is omitted and the components are coupled directly to each other using suitable connections.

Figure 7A:
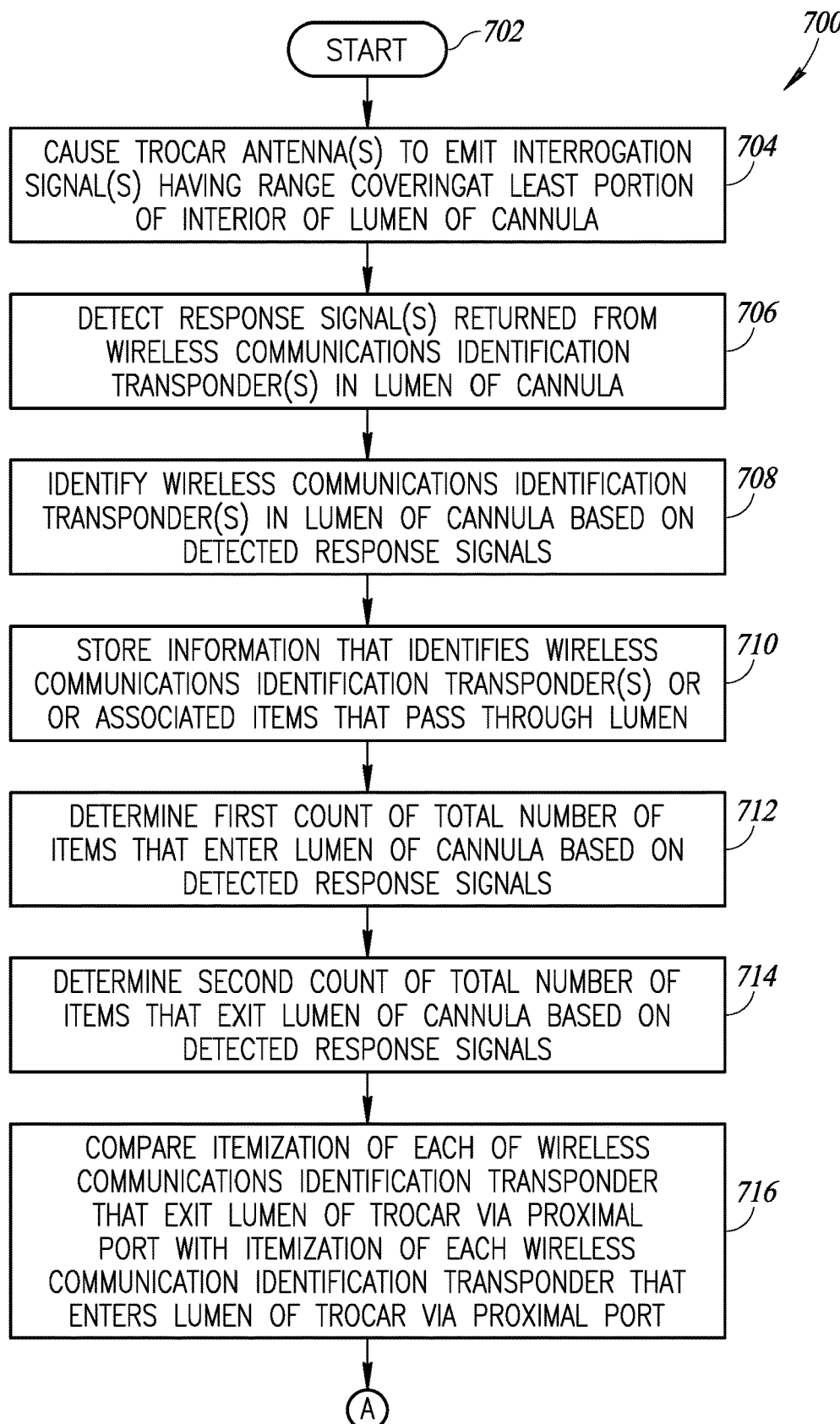
FIGS. 7A-7B are a flow diagram showing a workflow or method of operating a medical procedure object accounting system to account for, track or monitor medical procedure instruments and supplies, according to one illustrated embodiment, employing various of the apparatus or devices described in reference to FIGS. 1-6, according to at least one illustrated implementation.
Figure 7B:
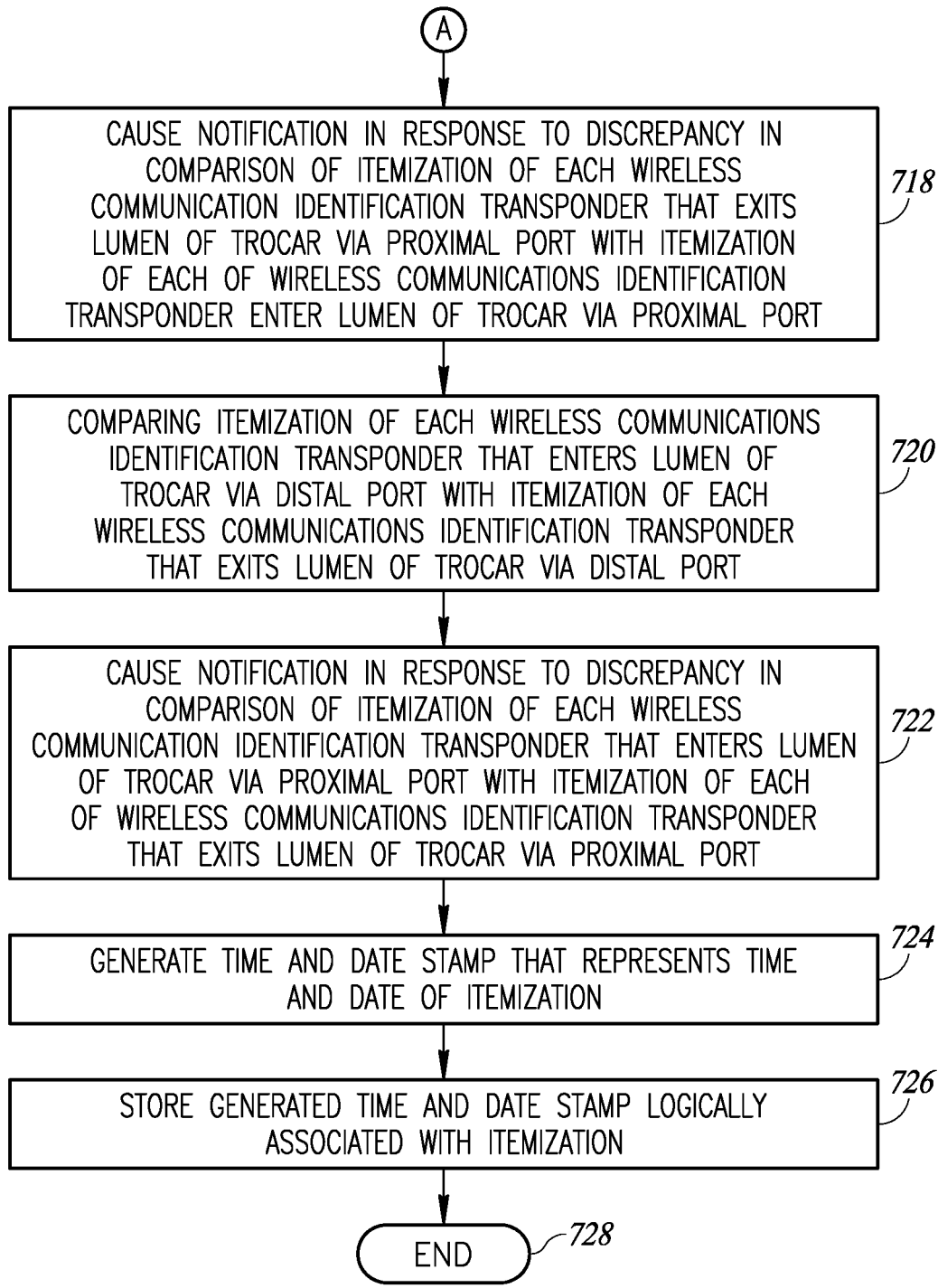

FIGS. 7A-7B show a method 700 of operating a medical procedure object accounting system to account for, track or monitor medical procedure instruments and supplies, according to one illustrated embodiment. The method 700 can, for example, be implemented by the structures of FIGS. 1A, 1B, 1C, and 1D which employs RFID interrogators or readers associated with a trocar or other medical or clinical procedure instrument.

The method 700 can be used as a standalone method, or can be employed along with, or even part of, the various other methods described herein.

The method 700 starts at 702, for example on power ON of one or more components (e.g., accounting system, RFID interrogators or readers, presence/absence interrogators or readers), on invocation of some calling program, routine, subprogram or function, or for example in response to detection of motion via a suitable motion sensor (e.g., one- or multi-axis accelerometer). Alternatively, the method may start in response to detection of an item (e.g., instrument or supply) entering the trocar, for instance via an entrance or proximal port of a lumen.

At 704, at least during a first period, one or more trocar RFID antenna(s) of an RFID interrogation system emit RFID interrogation signal(s) having a range that covers at least a portion of an interior of a lumen of a trocar or cannula. The RFID interrogation signals are typically in a first frequency range (e.g., UHF), which is typically a relatively higher frequency than a frequency of interrogation signals for dumb wireless transponders. Such can occur automatically, via autonomous control by an RFID interrogator, or alternatively via manual operation (e.g., activation of a switch or trigger) of an RFID interrogator by the personnel. Typically, the RFID interrogation system will emit RFID interrogation signal(s) via a number of associated trocar RFID antennas, for example positioned and/or oriented at or proximate an entrance or proximal end of the lumen and/or positioned and/or oriented at or proximate an exit or distal end of the lumen to provide limited coverage of a portion of the interior of the lumen of the trocar. In at least some implementations, interrogation can occur as instruments or supplies pass through a portion (e.g., annular portion) of the lumen, for instance an entrance or proximal port and/or an exit or distal port. In at least some implementations, such can occur by passing the instruments and supplies by a respective trocar RFID antenna of the RFID interrogation system, for example one by one. The first period may, for example, be at or proximate a start of the medical or clinical procedure.

At 706, during the first period, one or more RFID interrogators or readers detect RFID response signal(s) returned from wireless identification transponder(s) in or passing through the lumen of the trocar.

At 708, one or more RFID interrogators or readers identify wireless identification transponder(s) in or passing through the lumen of the trocar based on RFID response signals detected during the first period.

At 710, the RFID interrogators or readers or an accounting system adds item entries for each instrument and/or supply (e.g., automatic count in) to an inventory based on the various RFID response signal(s) detected during the first period, for instance in response to receipt of information from one or more RFID interrogators or readers. For example, the accounting system may update a field of a record associated with or corresponding to the particular instrument, supply or RFID transponder physically associated therewith. The inventory can be maintained locally or remotely.

The accounting system can, for example, itemize each of the wireless communications identification transponders and/or associated items that enter the lumen of the trocar via a proximal port (e.g., entrance, proximate the user). The accounting system can, for example, itemize each of the wireless communications identification transponders and/or associated items that exit the lumen of the trocar via the proximate port. The accounting system can, for example, itemize each of the wireless communications identification transponders and/or associated items that enter the lumen of the trocar via a distal port (e.g., exit, distal to the user). The accounting system can, for example, itemize each of the wireless communications identification transponders and/or associated items that exit the lumen of the trocar via the distal port (e.g., exit, proximate patient and obturator).

At 712, the RFID interrogation system or the accounting system can determine a first count of total number of items that enter lumen of cannula based on detected response signals.

At 714, the RFID interrogation system or the accounting system can determine a second count of total number of items that exit lumen of cannula based on detected response signals.

At 716, the RFID interrogation system or the accounting system can compare itemization of each of the wireless communications identification transponders that exits the lumen of the trocar via the proximal port with the itemization of each of the wireless communications identification transponders that enters the lumen of the trocar via the proximal port.

At 718, the RFID interrogation system or the accounting system can cause a notification to be provided in response to a discrepancy in the comparison of the itemization of each of the wireless communications identification transponders that exits the lumen of the trocar via the proximal port with the itemization of each of the wireless communications identification transponders that enters the lumen of the trocar via the proximal port. The notification can, for example, take the form of a visual and/or aural alert. Such can be provided via a display monitor, speakers and/or a heads up or head-worn device, e.g., a virtual reality or augmented reality head set. Such can alternatively and/or additionally be provided as an alert and/or notification on an indicator that is located on the trocar.

At 720, the RFID interrogation system or the accounting system can compare the itemization of each of the wireless communications identification transponders that enters the lumen of the trocar via the distal port with the itemization of each of the wireless communications identification transponders that exits the lumen of the trocar via the distal port.

At 722, the RFID interrogation system or the accounting system can cause notification to be provided in response to a discrepancy in the comparison of the itemization of each of the wireless communications identification transponders that enters the lumen of the trocar via the distal port with the itemization of each of the wireless communications identification transponders that exits the lumen of the trocar via the distal port. The notification can, for example, take the form of a visual and/or aural alert. Such can be provided via a display monitor, speakers and/or a heads up or head-worn device, e.g., a virtual reality or augmented reality head set. Such can alternatively and/or additionally be provided as an alert and/or notification on an indicator that is located on the trocar.

Optionally at 724, the accounting system can generate a time and date stamp that represents a time and date of the itemization.

Optionally at 726, the accounting system or some other component stores the time and date stamp associated with inventory in tamper-proof form. For example, the accounting system can generate a hash based on the accounting and inventory and time and date stamp and store the same, allowing such to be later validated by authorized parties.

The method 700 terminates at 728, for example until invoked again. In some implementations, the method 700 may be executed repeatedly, even continuously, or periodically or aperiodically. The method 700 can be implemented as multiple threads, for example via a multi-threaded processor.

Figure 8:
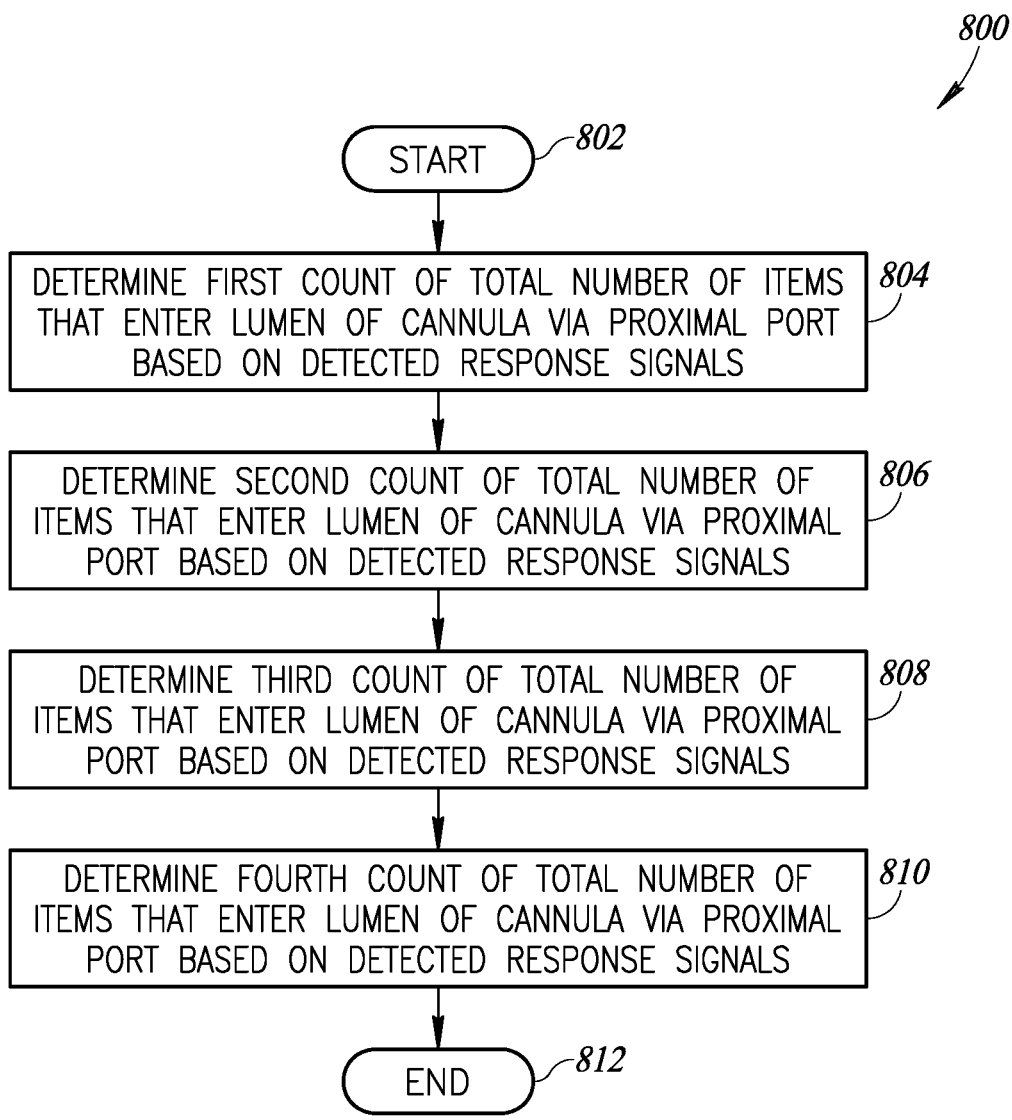
FIG. 8 is a flow diagram showing a workflow or method of operation in a medical or clinical environment according to at least one implementation, for example as part of the workflow or method of FIGS. 7A-7B.

FIG. 8 is a flow diagram showing a workflow or method of operation in a medical or clinical environment according to at least one implementation, for example as part of the workflow or method 700 of FIGS. 7A-7B.

The method 800 starts at 802. At 804, an RFID interrogation system or an accounting system determines a first count of a total number of items that enter the lumen of the cannula via a proximal port (e.g., entrance, proximate the user) based on the detected response signals. For example, the range of a first antenna positioned at or proximate the proximal port can be limited to cover an interior volume of the lumen at or proximate the proximal port without also covering an interior volume of the lumen at or proximate a proximal port. In some implementations, two spaced apart antennas (e.g., 102a and 102c; 102b and 102d; 102a and 102b) may be employed to detect a relative direction of travel of an item and associated RFID transponder in the trocar. The RFID interrogation system or an accounting system can, for example, determine direction (e.g., ingress or egress via the proximal port) of the item and associated RFID transponder based on a timing or sequence of detection of the given RFID transponder by each of the two antennas. Thus, if a given RFID transponder is detected by a first antenna relatively upstream (i.e., direction of flow is from the entrance or proximal port toward the exit or distal port) before detection by a relatively downstream one of the antennas, the item and associated RFID are passing in a first direction (e.g., advancing) along the lumen of the trocar. Conversely, if a given RFID transponder is detected by a relatively downstream one of the antennas before detection by a relatively upstream one of the antennas, the item and associated RFID are passing in a second direction (e.g., being withdrawn). In some implementations, two antennas can be located at or proximate respective ends of the trocar or lumen. In some implementations, two closely spaced antennas may be positioned at or proximate the proximal port, each of these antennas spaced relatively from one another. Additionally or alternatively, in some implementations, two closely spaced antennas may be positioned at or proximate the distal port, each of these antennas spaced relatively from one another.

At 806, the RFID interrogation system or the accounting system determines a second count of a total number of items that exit the lumen of the cannula via the proximal port based on the detected response signals.

At 808, the RFID interrogation system or the accounting system determine a third count of a total number of items that enter the lumen of the cannula via a distal port (e.g., exit, proximate patient and obturator) based on the detected response signals. For example, the range of a second antenna positioned at or proximate the distal port can be limited to cover an interior volume of the lumen at or proximate the distal port without also covering an interior volume of the lumen at or proximate the proximal port.

At 810, the RFID interrogation system or the accounting system determine a fourth count of a total number of items that exit the lumen of the cannula via the distal port based on the detected response signals.

The method 800 terminates at 812, for example until invoked again. In some implementations, the method 800 may be executed repeatedly, even continuously, or periodically or aperiodically. The method 800 can be implemented as multiple threads, for example via a multi-threaded processor.

Transponders useful for marking medical procedure related objects may take a variety of forms. Transponders capable of withstanding sterilization procedures would be particularly advantageous. A permanent memory type RFID transponder which retains information or data, for instance a unique identifier, and which is substantially gamma ray resistant and capable of being subjected to the relatively high temperatures often associated with sterilization may be formed from an antenna, passive power or backscatter circuit and a permanent memory circuit communicatively coupled to the antenna and powered via the passive power or backscatter circuit to transmit the contents of the permanent memory in response to power derived from an interrogation signal. The permanent memory circuit may advantageously take the form or may incorporate aspects of the permanent memory circuits described in one or more of U.S. Pat. Nos. 7,609,538; 7,471,541; 7,269,047; 7,042,722; 7,031,209; 6,992,925; 6,972,986; 6,956,258; 6,940,751; 6,898,116; 6,856,540; 6,822,888; 6,798,693; 6,791,891; 6,777,757; 6,766,960; 6,700,151; 6,671,040; 6,667,902; and 6,650,143, all of which are incorporated herein by reference in their entireties to the extent that such are not inconsistent with the other portions of present detailed description. Applicants have recognized that such permanent memory circuits may be resistant to gamma ray radiation, chemicals (e.g., peroxide) and/or high temperatures, and thus may be particularly suitable for use in manufacturing transponders for use in marking objects that will be subjected to the extremes of sterilization. The permanent memory type transponder may include a housing, shell or encapsulant. Such a permanent memory transponder may be particularly useful for marking gauze or sponges. Such a transponder may be attached to a medical procedure related object in any variety of fashions, including sewn to, sewn in, adhered via adhesives or heat or RF welding, riveted, tied to, via a snap, stapled, etc.

Various structures are referred to as shielded, that is shielded at least from certain radio frequencies or wavelengths and/or microwave frequencies or wavelength in the frequency ranges or wavelength ranges at which the wireless transponders and associated interrogators operate, i.e., frequency ranges or wavelength ranges of interrogation signals transmitted by the interrogators and/or frequency ranges or wavelength ranges of response signals returned by wireless transponders. The shield may be a Faraday cage, that sufficiently attenuates electromagnetic signals as to prevent communication between the interrogator(s) and the wireless transponder(s). The shield (e.g., Faraday cage) can comprise sheets and/or meshes of conductive material (e.g., aluminum, copper, silver, gold, mild steel), of sufficient conductivity, thickness, and geometry as to cause attenuation (e.g., 50 dB; 60 dB reduction via a silver coated nylon fabric; 85 dB reduction via aluminum foil, 120 dB reduction via Mu-copper foil of 0.12 mm thick) in the particular wavelength or frequency ranges of interest (e.g., 125 kHz, 13.5 MHz, 900 MHz, and 3.5-5.8 MHz). Where a mesh is employed, the holes or apertures of the mesh should have a characteristic dimension that is much smaller (e.g., ¼ wavelength) than the wavelength of the signal to be stopped (i.e., interrogation signal and/or response signal).

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other transponders and interrogation and detection systems, not necessarily the exemplary surgical object transponders and interrogation and detection systems generally described above.

Also for instance, many of the embodiments described herein, perform interrogation and detection of transponder tagged objects using multiple antennas. Successive ones of the antennas may be used to transmit an interrogation signal, while two or more antennas are monitored for a response to the interrogation signal. Such may provide significant advantages over more conventional methods, for example motion-based methods that employ motion (e.g., sweeping)

of an antenna (e.g., wand) over a patient. For instance, this allows the transmit and receive paths to the transponder to be different from one another (e.g., the transmit path is from a first antenna to a transponder, while the receive path is from the transponder to a second antenna). Hence, the path length to the transponder may be shortened in many configurations, thus improving the signal. For instance, when using a single antenna to both transmit an interrogation signal and to receive a response to the interrogation signal, the power of the received signal is equal to about the 6th root of the input power. However, when using multiple antennas to transmit and receive over the same area, interrogation path length in one direction may be shorter. Another advantage is that all scan time may be averaged, allowing a longer noise time averaging (e.g., 10 seconds) as opposed to motion-based scanning, where integration time may be limited (e.g., about 0.25 seconds per sample). Even further, a representative value of noise samples measured over a plurality of antennas may be employed to determine noise to be removed from noise plus signals received at one of the antennas, thereby advantageously lowering a noise floor and/or increasing range or performance. Thus, the various disclosed embodiments may provide significantly better performance.

While generally discussed in terms of trocars, the various teachings herein can be applied to other instruments, for example other medical instruments with channels or with tubular bodies (e.g., cylindrical, rectangular, and/or hexagonal tube), for instance syringes.

While generally discussed in terms of a passive wireless transponder, which requires an interrogation signal to derive electrical energy to power operation, for example to backscatter a response signal, such is not necessary to all implementations. For example, some implementations can employ an active transponder, with an onboard, consumable power source (e.g., chemical battery), which can emit signals from time-to-time (e.g., periodically) without any external stimulus (e.g., interrogation signals). Such implementations are of course subject to the power source being capable of operating over long times, even if the object to which the active wireless transponder is attached is not put into service for several years. Thus, most implementations will employ passive wireless transponders, and thus employ interrogation signals.

In some embodiments, a high speed LINUX-based microprocessor may be employed in the console. In some embodiments, an LCD touch screen may be employed as a user interface device. Some embodiments may include update-ready software images for new applications. Such may facilitate the automatic loading of instructions on detection of a new device. RF reading may be performed using a handheld wand, via antennas located at the various nursing stations, a standalone handheld RFID reader, and/or via antennas positioned to interrogate all or part of a body. A PDR log may be maintained. Information may be offloaded in a variety of fashions, for instance a memory stick, wireless data transfer, or printer. An optional monitor may be coupled to the presence/absence interrogator or reader to display video or other images. In some embodiment, one or more machine-readable symbol readers may be coupled to the presence/absence interrogator or reader to read machine-readable symbols and transfer read data to the console. In some embodiments, a reading or scanning device (e.g., handheld antenna, handheld RFID reader, machine-readable symbol readers, antenna position to reader items on various tables and stands or nursing stations) may be a USB device, which automatically uploads counting or accounting instructions (e.g., software) to a presence/absence interrogator or reader when communicatively coupled thereto. The reading or scanning device may be appropriate for use with aseptic techniques, for example via placement under a drape or otherwise covered, or having been sterilized (e.g., autoclave). The reader or scanning device may be an antenna suitable for interrogating RFID transponders or a reader suitable for interrogating RFID transponders. Such may be incorporated in a mat, dish, tray or packed coil apparatus. Such may be used as a check in and/check out apparatus to ensure management or accounting of objects in the medical procedure environment. A suitable antenna may be a coil that enables object reading in random orientations over specific portions of nurse management areas (e.g., instrument or supply tables or stands).

Also for instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Various exemplary methods or processes are described. It is noted that these exemplary methods or processes may include additional acts and/or may omit some acts. In some implementations, the acts of the various exemplary methods or processes may be performed in a different order and/or some acts may be executed or performed concurrently.

In addition, those skilled in the art will appreciate that the mechanisms of taught herein are capable of being distributed as a program product in a variety of forms, and that an illustrative embodiment applies equally regardless of the particular type of physical signal bearing media used to actually carry out the distribution. Examples of signal bearing media include, but are not limited to, the following: recordable type media such as floppy disks, hard disk drives, CD ROMs, digital tape, and computer memory.

The various embodiments described above can be combined to provide further embodiments. To the extent not inconsistent with the teachings herein, all U.S. patents, U.S. patent application publications, U.S. patent applications, foreign patents, foreign patent applications and non-patent publications commonly owned with this patent application and referred to in this specification and/or listed in the Application Data Sheet including: U.S. Pat. No. 6,026,818, issued Feb. 22, 2000; U.S. Patent Publication No. US 2004/0250819, published Dec. 16, 2004; U.S. Pat. No. 8,710,957, issued Apr. 29, 2014; U.S. Pat. No. 7,898,420, issued Mar. 1, 2011; U.S. Pat. No. 7,696,877, issued Apr. 13, 2010; U.S. Pat. No. 8,358,212, issued Jan. 22, 2013; U.S.

Pat. No. 8,111,162, issued Feb. 7, 2012; U.S. Pat. No. 8,354,931, issued Jan. 15, 2013; U.S. Patent Publication No. US 2010/0108079, published May 6, 2010; U.S. Patent Publication No. US 2010/0109848, published May 6, 2010; U.S. Patent Publication No. US 2011/0004276, published Jan. 6, 2011; U.S. Patent Publication No. US 2011/0181394, published Jul. 28, 2011; U.S. Patent Publication No. US 2013/0016021, published Jan. 17, 2013; PCT Patent Publication No. WO 2015/152975, published Oct. 8, 2015; U.S. Provisional patent application Ser. No. 62/143,726 filed Apr. 6, 2015; U.S. Provisional patent application Ser. No. 62/182,294 filed Jun. 19, 2015; U.S. Provisional patent application Ser. No. 62/164,412 filed May 20, 2015; U.S. Non-Provisional patent application Ser. No. 14/523,089 filed Oct. 24, 2014; U.S. Non-Provisional patent application Ser. No. 14/327,208 filed Jul. 9, 2014; U.S. Non-Provisional patent application Ser. No. 15/003,515 filed Jan. 21, 2016; U.S. Non-Provisional patent application Ser. No. 15/003,524 filed Jan. 21, 2016; U.S. Non-Provisional patent application Ser. No. 15/052,125 filed Feb. 24, 2016; U.S. Non-Provisional patent application Ser. No. 15/053,965 filed Feb. 25, 2016; U.S. Provisional patent application Ser. No. 62/360,864 filed Jul. 11, 2016 and entitled "METHOD AND APPARATUS TO ACCOUNT FOR TRANSPONDER TAGGED OBJECTS USED DURING CLINICAL PROCEDURES, EMPLOYING A SHIELDED RECEPTACLE"; U.S. Provisional patent application Ser. No. 62/360,866 filed Jul. 11, 2016 and entitled "METHOD AND APPARATUS TO ACCOUNT FOR TRANSPONDER TAGGED OBJECTS USED DURING CLINICAL PROCEDURES EMPLOYING A SHIELDED RECEPTACLE WITH ANTENNA"; and U.S. Provisional patent application Ser. No. 62/360,868 filed Jul. 11, 2016 and entitled "METHOD AND APPARATUS TO ACCOUNT FOR TRANSPONDER TAGGED OBJECTS USED DURING CLINICAL PROCEDURES, FOR EXAMPLE INCLUDING COUNT IN AND/OR COUNT OUT AND PRESENCE DETECTION", are each incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An apparatus for use in clinical environments, the apparatus comprising:
a trocar, the trocar having a cannula with a proximal end and a distal end, the cannula which delineates a lumen therethrough that extends from the proximal end to the distal end, with a proximal port at the proximal end thereof which provides access to an interior of the lumen from an exterior of the cannula and with a distal port at the distal end thereof which provides access to the interior of the lumen from the exterior of the cannula,
wherein the trocar further includes an obturator that movingly extends through the cannula with a piercing tip located proximate the distal end;
a first trocar antenna coupled to the trocar and oriented to provide coverage of the proximal port and all wireless communications identification transponders passing through the proximal port;
a second trocar antenna coupled to the trocar and oriented to provide coverage of the distal port and all wireless communications identification transponders passing through the distal port;
a third trocar antenna coupled to the trocar, located at or proximate the proximal port and being spaced longitudinally with respect to the first trocar antenna;
a fourth trocar antenna coupled to the trocar, located at or proximate the distal port and being spaced longitudinally with respect to the first trocar antenna,
wherein the longitudinal separation between the first and third trocar antennas facilitates determination of a direction of travel of an object passing through the proximal port of the cannula, and
wherein the longitudinal separation between the second and fourth trocar antennas facilitates determination of a direction of travel of an object passing through the distal port of the cannula;
at least one indicator communicatively coupleable to receive signals that are representative of wireless communications transponders that pass through the lumen of the cannula, if any, the at least one indicator physically coupled to the trocar and positioned and oriented to provide at least one human-perceptible indication that represents at least one of: a count of a number of the wireless communications transponders that have entered the lumen of the cannula, a count of a number of the wireless communications transponders that have exited the lumen of the cannula, a sum of a number of the wireless communications transponders that have entered the lumen of the cannula and a number of the wireless communications transponders that have exited the lumen of the cannula, or a notification of a discrepancy in a number of the wireless communications transponders that have entered the lumen of the cannula and a number of the wireless communications transponders that have exited the lumen of the cannula,
wherein the at least one indicator is configured to display:
a first number that corresponds to the number of RFID transponders that enter the lumen of the cannula through the proximal port,
a second number that corresponds to the number of RFID transponders that exit the lumen of the cannula through the distal port, and
a combined number, wherein the combined number is configured to indicate a sum of a number of RFID transponders and/or dumb wireless transponders that enter the lumen of the cannula and a number of RFID transponders and/or dumb wireless transponders that exit the lumen of the cannula.

2. The apparatus of claim 1, wherein the piercing tip of the obturator is conical in shape.

3. The apparatus of claim 2, wherein the piercing tip of the obturator occludes an entirety of the lumen of the cannula.

4. An apparatus for use in clinical environments, the apparatus comprising:
a trocar, the trocar having a cannula with a proximal end and a distal end, the cannula which delineates a lumen therethrough that extends from the proximal end to the distal end, with a proximal port at the proximal end thereof which provides access to an interior of the lumen from an exterior of the cannula and with a distal port at the distal end thereof which provides access to the interior of the lumen from the exterior of the cannula, wherein the trocar further includes an obturator that movingly extends through the cannula with a piercing tip located proximate the distal end;

a first trocar antenna coupled to the trocar and oriented to provide coverage of the proximal port and all wireless communications identification transponders passing through the proximal port;

a second trocar antenna coupled to the trocar and oriented to provide coverage of the distal port and all wireless communications identification transponders passing through the distal port;

a third trocar antenna coupled to the trocar, located at or proximate the proximal port and being spaced longitudinally with respect to the first trocar antenna;

a fourth trocar antenna coupled to the trocar, located at or proximate the distal port and being spaced longitudinally with respect to the first trocar antenna, wherein the longitudinal separation between the first and third trocar antennas facilitates determination of a direction of travel of an object passing through the proximal port of the cannula, and wherein the longitudinal separation between the second and fourth trocar antennas facilitates determination of a direction of travel of an object passing through the distal port of the cannula;

at least one indicator communicatively coupleable to receive signals that are representative of wireless communications transponders that pass through the lumen of the cannula, if any, the at least one indicator physically coupled to the trocar and positioned and oriented to provide at least one human-perceptible indication that represents at least one of: a count of a number of the wireless communications transponders that have entered the lumen of the cannula, a count of a number of the wireless communications transponders that have exited the lumen of the cannula, a sum of a number of the wireless communications transponders that have entered the lumen of the cannula and a number of the wireless communications transponders that have exited the lumen of the cannula, or a notification of a discrepancy in a number of the wireless communications transponders that have entered the lumen of the cannula and a number of the wireless communications transponders that have exited the lumen of the cannula, wherein the at least one indicator is disposed between the third and fourth trocar antennas.

5. The apparatus of claim 4, wherein the piercing tip of the obturator is conical in shape.

6. The apparatus of claim 5, wherein the piercing tip of the obturator occludes an entirety of the lumen of the cannula.

* * * * *